(12) United States Patent
Buckley et al.

(10) Patent No.: US 12,125,567 B2
(45) Date of Patent: Oct. 22, 2024

(54) SYSTEM AND METHOD FOR PATIENT DATA PROCESSING DURING DIAGNOSIS AND THERAPY

(71) Applicant: ResMed Inc., San Diego, CA (US)

(72) Inventors: Mark David Buckley, Sydney (AU); Linda Elizabeth Laidlaw, Sydney (AU)

(73) Assignee: ResMed Inc., San Diego, CA (US)

( * ) Notice: Subject to any disclaimer, the term of this patent is extended or adjusted under 35 U.S.C. 154(b) by 15 days.

(21) Appl. No.: 17/886,957

(22) Filed: Aug. 12, 2022

(65) Prior Publication Data

US 2022/0383999 A1 Dec. 1, 2022

Related U.S. Application Data

(63) Continuation of application No. 15/026,308, filed as application No. PCT/AU2014/050268 on Oct. 3, 2014, now Pat. No. 11,450,414.

(30) Foreign Application Priority Data

Oct. 4, 2013 (AU) .................................. 2013903830

(51) Int. Cl.
*G16H 10/60* (2018.01)
*A61B 5/08* (2006.01)
(Continued)

(52) U.S. Cl.
CPC ........... *G16H 10/60* (2018.01); *A61B 5/0826* (2013.01); *A61M 16/0057* (2013.01);
(Continued)

(58) Field of Classification Search
CPC ........ G16H 10/60; G16H 40/40; G16H 40/67; G16H 20/40; A61B 5/0826;
(Continued)

(56) References Cited

U.S. PATENT DOCUMENTS 4,782,832 A 11/1988 Trimble et al.
7,831,444 B2 11/2010 Brown et al.
(Continued)

FOREIGN PATENT DOCUMENTS

AU 2012261537 A1 12/2012
JP 2004280807 A 10/2004
(Continued)

OTHER PUBLICATIONS

European Search Report for Application No. EP21209044 dated Apr. 4, 2022.
(Continued)

*Primary Examiner* — Robert A Sorey
*Assistant Examiner* — Kimberly A. Sass
(74) *Attorney, Agent, or Firm* — Botos Churchill IP Law LLP

(57) ABSTRACT

A system and method for patient data processing during diagnosis and therapy of a patient's sleep disorder breathing. The system and method includes providing diagnostic providers and therapy device providers with a simple and fast way to generate a clinical diagnosis from a diagnostic device and to transfer that patient's record and diagnostic data to the therapy provider responsible for the patient's ongoing care. The patient may be automatically assigned therapy devices having predetermined therapy settings that are based on the patient's record and diagnostic data.

18 Claims, 21 Drawing Sheets

(51) Int. Cl.
  *A61M 16/00*  (2006.01)
  *A61M 16/06*  (2006.01)
  *A61M 16/16*  (2006.01)
  *G16H 40/40*  (2018.01)
  *G16H 40/67*  (2018.01)

(52) U.S. Cl.
  CPC .... *A61M 16/0622* (2014.02); *A61M 16/0666* (2013.01); *A61M 16/16* (2013.01); *G16H 40/40* (2018.01); *G16H 40/67* (2018.01)

(58) Field of Classification Search
  CPC .......... A61M 16/0057; A61M 16/0622; A61M 16/0666; A61M 16/16; Y02A 90/10
  See application file for complete search history.

(56) References Cited

U.S. PATENT DOCUMENTS

| | | | |
|---|---|---|---|
| 8,381,724 B2 * | 2/2013 | Bowen | A61M 16/0063 128/204.21 |
| 2002/0026223 A1 * | 2/2002 | Riff | A61N 1/37252 607/27 |
| 2003/0208465 A1 | 11/2003 | Yurko et al. | |
| 2007/0136095 A1 | 6/2007 | Weinstein | |
| 2008/0114689 A1 | 5/2008 | Psynik | |
| 2009/0044808 A1 | 2/2009 | Guney et al. | |
| 2009/0229610 A1 | 9/2009 | Oates et al. | |
| 2010/0000534 A1 | 1/2010 | Kooij et al. | |
| 2010/0094656 A1 | 4/2010 | Conant | |
| 2011/0191343 A1 | 8/2011 | Heaton et al. | |
| 2012/0068847 A1 | 3/2012 | Pirzada | |
| 2012/0247472 A1 * | 10/2012 | Lynch, Jr. | A61M 16/0051 128/204.23 |
| 2014/0058755 A1 * | 2/2014 | Macoviak | G06Q 10/10 705/2 |

FOREIGN PATENT DOCUMENTS

| | | |
|---|---|---|
| JP | 2005535360 A | 11/2005 |
| JP | 2009172383 A | 8/2009 |
| JP | 2010509659 A | 3/2010 |
| JP | 2010113504 A | 5/2010 |
| WO | 1998004310 A1 | 2/1998 |
| WO | 2001032069 | 5/2001 |
| WO | 2004073778 A1 | 9/2004 |
| WO | 2005063328 A1 | 7/2005 |
| WO | 2006074513 A1 | 7/2006 |
| WO | 2006130903 A1 | 12/2006 |
| WO | 2008089204 A1 | 7/2008 |
| WO | 2009052560 A1 | 4/2009 |
| WO | 2010135785 A1 | 12/2010 |
| WO | 2012006339 A2 | 1/2012 |
| WO | 2012168848 A1 | 12/2012 |
| WO | 2008057952 A2 | 5/2019 |

OTHER PUBLICATIONS

Japanese Office Action for Appl. 2016-519843 dated Aug. 15, 2018.
JP Notice of Allowance issued Dec. 24, 2020 for Japanese Patent Application No. 2016-519843.
Office Action for Japanese Patent Application No. 2020-167491, Aug. 6, 2021.
Supplementary European Search Report for Application No. EP14850419, dated May 4, 2017.
The International Search Report and The Written Opinion for International Application No. PCT/AU2014/050268 dated Dec. 5, 2014.
The International Search Report for International Application No. PCT/AU2014/050268 dated May 4, 2015.
The Written Opinion for International Application No. PCT/AU2014/050268 dated Aug. 7, 2015.
Office Action issued in corresponding Japanese Patent Application No. 2022-121547 mailed Oct. 3, 2023, 4 pages.

* cited by examiner

SYSTEM AND METHOD FOR PATIENT DATA PROCESSING DURING DIAGNOSIS AND THERAPY

CROSS-REFERENCE TO RELATED APPLICATIONS

This application is a continuation of U.S. application Ser. No. 15/026,308, filed on Mar. 31, 2016, which is a national phase entry under 35 U.S.C. § 371 of International Application No. PCT/AU2014/050268 filed Oct. 3, 2014, published in English, which claims priority from Australian Application No. 2013903830 filed Oct. 4, 2013, all of which are incorporated herein by reference.

1 BACKGROUND

1.1 Field of the Technology present technology relates to the diagnosis and treatment of respiratory-related disorders.

1.1 Description of the Related Art 1.1.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "Respiratory Physiology", by John B. West, Lippincott Williams & Wilkins, 9th edition published 2011.

A range of respiratory disorders exist. Some examples of respiratory disorders include: Obstructive Sleep Apnea (OSA), Cheyne Stokes Respiration (CSR), Obesity Hyperventilation Syndrome (OHS), Chronic Obstructive Pulmonary Disease (COPD), Neuromuscular Disease (NMD) or chest wall disorders.

Otherwise healthy individuals may take advantage of systems and devices to prevent respiratory disorders from arising.

1.1.2 Diagnosis and Therapy

Patients' interaction with the health system generally comprises two main stages or phases—a diagnostic stage and a treatment (also referred to as "therapy") stage.

During the diagnostic stage a patient is tested and the patient's condition is diagnosed. In the area of sleep and respiratory disorders, the diagnostic providers, as well as the therapy providers can be qualified medical practitioners, also referred to as physicians or doctors, or assisting practitioners referred to as clinicians. Instead of conducting a sleep test in a sleep lap or sleep clinic, a diagnostic providers increasingly use portable take home testing devices to diagnose patients with sleep disorder breathing. Once the patient is diagnosed, they may be put on a suitable therapy.

The application of the respiratory therapy defines the therapy stage, during which the patient is treated for the purpose of managing the patient's condition and/or ameliorating its symptoms. The services to supply the CPAP devices used for such therapy and monitor the progress of the patient's therapy may be provided by a therapy provider organisation, such as a Home Medical Equipment (HME) company. A therapy provider from the therapy provider company, such as a therapy clinician, may configure the device as per directions from the prescription, and put the patient on a program to monitor their ongoing adherence to therapy and the patient's therapy progress. For example, patients suffering from sleep apnea may be diagnosed via a Home Sleep Test by a diagnostic provider and prescribed a therapy device, such as a continuous positive airway pressure ("CPAP") device, for home respiratory therapy that is prescribed to operate at a particular pressure. The therapy provider for this patient will provide the device and set the required pressure and other settings. Alternatively, the therapy device may be configured for automatic initial setup, based on the prescription settings in the diagnostic prescription issued by the diagnostic provider.

Thus, the therapy provider may be responsible for setting the patient for therapy. This may involve selection of a treatment mask, humidifier, conduits and other accessories, which may or may not be specified in the prescription issued by the diagnostic provider. Apart from the initial setup, the therapy provider will also monitor the therapy data from the patient therapy sessions. If the patient's therapy progress is unsatisfactory or there are other problems with the therapy, the therapy provider may refer the patient back to the diagnostic provider for review and modification to the therapy.

Insurance companies, or other assessing or reimbursing entity computer 103, often require evidence that the patient has been diagnosed in an appropriate manner before paying for the diagnosis. In order for a determination to be made of whether a patient was appropriately diagnosed, a diagnostic provider will need to present the appropriate data from a Home Sleep Test device (which will also be referred to in this specification as a diagnostic device) and a diagnosis needs to be made available that is signed by a qualified physician. Furthermore, insurance companies often want to track whether a patient once diagnosed with a medical condition successfully proceeds to and remains on the therapy for which they are prescribed. This process can be inefficient and time consuming, with very poor patient traceability during the transfer of the patient between the diagnostic and therapy provider. The transfer may be inconvenient and disruptive, because multiple records of the patient (e.g. one during the diagnostic stage patient management and another one during the therapy stage) are being created on different software packages and in different software environments. The communication between the two stages also currently involves paper records and/or faxed documents. This may cause inconvenience to the patients and the diagnostic and therapy service providers, as well as cause errors in the patient's records.

1.1.3 Systems

A therapy system may comprise a Respiratory Pressure Therapy Device (RPT device), an air circuit, a humidifier, a patient interface, and data management.

1.1.4 Patient Interface

A patient interface may be used to interface respiratory equipment to its user, for example by providing a flow of breathable gas. The flow of breathable gas may be provided via a mask to the nose and/or mouth, a tube to the mouth or a tracheostomy tube to the trachea of the user. Depending upon the therapy to be applied, the patient interface may form a seal, e.g. with a face region of the patient, to facilitate the delivery of gas at a pressure at sufficient variance with ambient pressure to effect therapy, e.g. a positive pressure of about 10 cmH2O. For other forms of therapy, such as the delivery of oxygen, the patient interface may not include a seal sufficient to facilitate delivery to the airways of a supply of gas at a positive pressure of about 10 cmH2O.

The design of a patient interface presents a number of challenges. The face has a complex three-dimensional shape. The size and shape of noses varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use and uncomfortable especially when worn for long periods of time or when a patient is unfamiliar with a system. For example, masks designed solely for aviators, mask designed as part of personal protection equipment (e.g. filter masks), SCUBA masks or for the administration of anaesthetics may be tolerable for their original application, but nevertheless be undesirably uncomfortable to be worn for extended periods of time, e.g. several hours. This is even more so if the mask is to be worn during sleep.

Nasal CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g. difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, masks for delivery of nasal CPAP during sleep form a distinct field.

1.1.4.1 Seal-Forming Portion

Patient interfaces may include a seal-forming portion. Since it is in direct contact with the patient's face, the shape and configuration of the seal-forming portion can have a direct impact the effectiveness and comfort of the patient interface.

A patient interface may be partly characterised according to the design intent of where the seal-forming portion is to engage with the face in use. In one form of patient interface, a seal-forming portion may comprise two sub-portions to engage with respective left and right nares. In one form of patient interface, a seal-forming portion may comprise a single element that surrounds both nares in use. Such single element may be designed to for example overlay an upper lip region and a nasal bridge region of a face. In one form of patient interface a seal-forming portion may comprise an element that surrounds a mouth region in use, e.g. by forming a seal on a lower lip region of a face. In one form of patient interface, a seal-forming portion may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming portion that may be effective in one region of a patient's face may be in appropriate in another region, e.g. because of the different shape, structure, variability and sensitivity regions of the patient's face. For example, a seal on swimming goggles that overlays a patient's forehead may not be appropriate to use on a patient's nose.

Certain seal-forming portions may be designed for mass manufacture such that one design fit and be comfortable and effective for a wide range of different face shapes and sizes. To the extent to which there is a mismatch between the shape of the patient's face, and the seal-forming portion of the mass-manufactured patient interface, one or both must adapt in order for a seal to form.

One type of seal-forming portion extends around the periphery of the patient interface, and is intended to seal against the user's face when force is applied to the patient interface with the seal-forming portion in confronting engagement with the user's face. The seal-forming portion may include an air or fluid filled cushion, or a moulded or formed surface of a resilient seal element made of an elastomer such as a rubber. With this type of seal-forming portion, if the fit is not adequate, there will be gaps between the seal-forming portion and the face, and additional force will be required to force the patient interface against the face in order to achieve a seal.

Another type of seal-forming portion incorporates a flap seal of thin material so positioned about the periphery of the mask so as to provide a self-sealing action against the face of the user when positive pressure is applied within the mask. Like the previous style of seal forming portion, if the match between the face and the mask is not good, additional force may be required to effect a seal, or the mask may leak. Furthermore, if the shape of the seal-forming portion does not match that of the patient, it may crease or buckle in use, giving rise to leaks.

Another type of seal-forming portion may comprise a friction-fit element, e.g. for insertion into a naris.

Another form of seal-forming portion may use adhesive to effect a seal. Some patients may find it inconvenient to constantly apply and remove an adhesive to their face.

A range of patient interface seal-forming portion technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT nasal pillows mask, SWIFT II nasal pillows mask, SWIFT LT nasal pillows mask, SWIFT FX nasal pillows mask and LIBERTY full-face mask. The following patent applications, assigned to ResMed Limited, describe nasal pillows masks: International Patent Application WO2004/073,778 (describing amongst other things aspects of ResMed SWIFT nasal pillows), US Patent Application 2009/0044808 (describing amongst other things aspects of ResMed SWIFT LT nasal pillows); International Patent Applications WO 2005/063, 328 and WO 2006/130,903 (describing amongst other things aspects of ResMed LIBERTY full-face mask); International Patent Application WO 2009/052,560 (describing amongst other things aspects of ResMed SWIFT FX nasal pillows).

1.1.4.2 Positioning and Stabilising

A seal-forming portion of a patient interface used for positive air pressure therapy is subject to the corresponding force of the air pressure to disrupt a seal. Thus a variety of techniques have been used to position the seal-forming portion, and to maintain it in sealing relation with the appropriate portion of the face.

One technique is the use of adhesives. See for example US Patent publication US 2010/0000534.

Another technique is the use of one or more straps and stabilising harnesses. Many such harnesses suffer from being one or more of ill-fitting, bulky, uncomfortable and awkward to use.

1.1.5 Respiratory Pressure Therapy (RPT) Device

One known RPT device used for treating sleep disordered breathing is the S9 Sleep Therapy System, manufactured by ResMed. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD. RPT devices have also been known as flow generators.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit.

RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

RPT devices typically also include an inlet filter, various sensors and a microprocessor-based controller. A blower may include a servo-controlled motor, a volute and an impeller. In some cases a brake for the motor may be implemented to more rapidly reduce the speed of the blower so as to overcome the inertia of the motor and impeller. The braking can permit the blower to more rapidly achieve a lower pressure condition in time for synchronization with expiration despite the inertia. In some cases the pressure generator may also include a valve capable of discharging generated air to atmosphere as a means for altering the pressure delivered to the patient as an alternative to motor speed control. The sensors measure, amongst other things, motor speed, mass flow rate and outlet pressure, such as with a pressure transducer or the like. The controller may include data storage capacity with or without integrated data retrieval and display functions.

Table of noise output levels of prior devices (one specimen only, measured using test method specified in ISO3744 in CPAP mode at 10 cmH$_2$O).

| Device name | A-weighted sound power level dB(A) | Year (approx.) |
| --- | --- | --- |
| C-Series Tango | 31.9 | 2007 |
| C-Series Tango with Humidifier | 33.1 | 2007 |
| S8 Escape II | 30.5 | 2005 |
| S8 Escape II with H4i Humidifier | 31.1 | 2005 |
| S9 AutoSet | 26.5 | 2010 |
| S9 AutoSet with H5i Humidifier | 28.6 | 2010 |

1.1.6 Humidifier

Delivery of a flow of breathable gas without humidification may cause drying of airways. Medical humidifiers are used to increase humidity and/or temperature of the flow of breathable gas in relation to ambient air when required, typically where the patient may be asleep or resting (e.g. at a hospital). As a result, a medical humidifier is preferably small for bedside placement, and it is preferably configured to only humidify and/or heat the flow of breathable gas delivered to the patient without humidifying and/or heating the patient's surroundings. Room-based systems (e.g. a sauna, an air conditioner, an evaporative cooler), for example, may also humidify air that is breathed in by the patient, however they would also humidify and/or heat the entire room, which may cause discomfort to the occupants.

The use of a humidifier with a flow generator or RPT device and the patient interface produces humidified gas that minimizes drying of the nasal mucosa and increases patient airway comfort. In addition, in cooler climates warm air applied generally to the face area in and about the patient interface is more comfortable than cold air.

Respiratory humidifiers are available in many forms and may be a standalone device that is coupled to a respiratory apparatus via an air circuit, is integrated with or configured to be coupled to the relevant respiratory apparatus. While known passive humidifiers can provide some relief, generally a heated humidifier may be used to provide sufficient humidity and temperature to the air so that the patient will be comfortable. Humidifiers typically comprise a water reservoir or tub having a capacity of several hundred milliliters (ml), a heating element for heating the water in the reservoir, a control to enable the level of humidification to be varied, a gas inlet to receive gas from the flow generator or RPT device, and a gas outlet adapted to be connected to an air circuit that delivers the humidified gas to the patient interface.

Heated passover humidification is one common form of humidification used with a RPT device. In such humidifiers the heating element may be incorporated in a heater plate which sits under, and is in thermal contact with, the water tub. Thus, heat is transferred from the heater plate to the water reservoir primarily by conduction. The air flow from the RPT device passes over the heated water in the water tub resulting in water vapour being taken up by the air flow. The ResMed H4i™ and H5i™ Humidifiers are examples of such heated passover humidifiers that are used in combination with ResMed S8 and S9 CPAP devices respectively.

Other humidifiers may also be used such as a bubble or diffuser humidifier, a jet humidifier or a wicking humidifier. In a bubble or diffuser humidifier the air is conducted below the surface of the water and allowed to bubble back to the top. A jet humidifier produces an aerosol of water and baffles or filters may be used so that the particles are either removed or evaporated before leaving the humidifier. A wicking humidifier uses a water absorbing material, such as sponge or paper, to absorb water by capillary action. The water absorbing material is placed within or adjacent at least a portion of the air flow path to allow evaporation of the water in the absorbing material to be taken up into the air flow.

An alternative form of humidification is provided by the ResMed HumiCare™ D900 humidifier that uses a Counter-Stream™ technology that directs the air flow over a large surface area in a first direction whilst supplying heated water to the large surface area in a second opposite direction. The ResMed HumiCare™ D900 humidifier may be used with a range of invasive and non-invasive ventilators.

2 BRIEF SUMMARY OF THE TECHNOLOGY

The present technology relates to the diagnosis and treatment of sleep disorder breathing patients and related respiratory insufficiencies. Currently, the diagnostic stage and the therapy stage of patient management are somewhat disconnected and incoherent. What is needed is an integrated electronic system which links the diagnostic provider and therapy provider to the same patient database, and allows for easy generation, management, and transfer of a patient's diagnostic information directly to the prescribed flow generator (which will also be referred to in herein as a therapy device).

The present technology therefore relates to a method and system for an integrated processing and management of the patient data during the diagnostic and therapy stages. In particular, the described system provides diagnostic providers and therapy device providers with a simple and fast way to generate a clinical diagnosis from a diagnostic device and to transfer that patient's record and diagnostic data directly to the therapy provider responsible for the patient's ongoing care.

In accordance with one aspect of the technology, a server contains memory configured to store medical device data, and a processor in communication with the memory.

The processor is configured to receive diagnostic and therapy data for a plurality of medical device users, and to process diagnostic report data and therapy device usage data. A successful download of data may be based on whether the received diagnostic data from the device contains a predetermined duration of recording information and conforms to acceptable clinical ranges. Therapy compliance may be based on whether the received medical device usage data satisfies predetermined usage criteria, such as a number of hours of continuous usage or another predetermined criterion.

The processor is also configured to receive a request from the diagnostic provider or health providers for the diagnostic stage, as well as a compliance status for one or more of the patients using medical devices, and to transfer access to those patients from one provider to another.

In accordance with another aspect of the technology, a medical device can either be a Diagnostic Home Sleep Testing Device or a Therapy Device (e.g. a Flow Generator) used for respiratory therapy. In addition, the memory of the server may be further configured to store device identifiers, e.g., a unique ID number, wherein the medical device data for each of the plurality of medical device users includes a device identifier, which may be a unique device identifier, and wherein the processor of the server is further configured to associate the medical device usage data with a medical device user based on the received device identifiers.

In another aspect of the technology, the server's processor is further configured to regenerate medical device diagnostic data from at least one of the plurality of medical device users, based on a user determined change in analysis parameters.

In another aspect, a clinical diagnostic summary report may be provided, the report being of a format that allows an assessing entity to accept the report as verification of diagnosis. For example, the report may contain summary statistics from the diagnostic test data, a physician's interpretation of the test results and an electronic signature, as proof of review or acceptance.

In another aspect, a prescription based on a clinical diagnostic report may be provided. The prescription may be of a format that allows a therapy provider to supply a device, configure it for therapy and begin monitoring a schedule for reimbursement. For example, the prescription may contain a specified therapy device (e.g. CPAP), an itemised list of accessories (e.g. mask type), pressure settings for the device and an electronic signature. This document may be used by a Therapy Provider to legally supply the patient with the listed therapy items.

In another aspect of the technology, diagnostic and compliance indications are generated and displayed as selectable icons on the screen of a user.

In another aspect, a compliance report may be provided. The report may be of a format that allows an assessing entity to accept the report as verification of compliance. For example, the report may contain a numerical or graphical indication of compliance.

In another aspect of the technology, a healthcare professional associated with a diagnostic provider may access a website and select on the website one or more medical device users (patients) for which diagnostic information is available. The user may then select a therapy provider from a list of eligible organizations within the system and send the selected patients' diagnostic information to the selected organization. A user within the therapy provider will then receive a notification of the availability of diagnostic information for each of the one or more transferred medical device users, as well as the prescription information required to set up the patients on therapy.

In accordance with another aspect, a method for patient data processing during diagnosis and therapy of sleep disorder breathing may be performed. The method may include generating, by one or more computing devices, an electronic patient record for a patient; during a diagnostic stage of the patient, storing, by the one or more computing devices, diagnostic-related data in the electronic patient record; providing, by the one or more computing devices, a diagnostic medical practitioner with access to the electronic patient record; during a therapy stage of the patient, providing, by the one or more computing devices, a treating medical practitioner with access to the electronic patient record; and updating, by the one or more computing devices, the electronic patient record to include therapy-related data.

In another aspect, the method may include storing at least one of reports and prescriptions, generated during either the diagnostic stage or the therapy stage, in the electronic patient record. When the diagnostic stage is at an end, the treating medical practitioner is notified and provided access to at least one of diagnostic data and prescription data of the patient. Therapy settings from a therapy prescription may be retrieved from the electronic patient record and used to automatically configure a therapy device for the patient. The automatic configuration may be effected by way of a network connection or a memory card. In addition, the data storage, processing, and access during the diagnostic stage and the therapy stage are performed on a single software platform and on a single physical system of servers.

Once the electronic patient record is created, medical practitioners associated with either the diagnostic stage or the therapy stage may be provided access to the electronic patient record during both the diagnostic stage and the therapy stage. In addition, the diagnostic stage may include receiving data from a diagnostic device and the therapy stage may include receiving data from a therapy medical device, the therapy medical device being a flow generator for respiratory therapy.

In accordance with another aspect, a disclosed method may include receiving, by one or more computing devices, medical device data for a plurality of medical device users; storing, by the one or more computing devices, the medical device data; determining, by the one or more computing devices, whether to process the medical device data as diagnostic information or as compliance information, based on a predetermined criterion related to identification data of the medical devices; if the medical device data is processed as diagnostic data, generating, by the one or more computing devices, diagnostic information based on predetermined analysis criteria; enabling, by the one or more computing devices, an electronic transfer of at least one of an clinical diagnosis report to an associated therapy provider, wherein the diagnosis report is based on the diagnostic information; and transmitting, by the one or more computing devices, a therapy settings to a therapy device associated with the diagnosis report.

In accordance with another aspect, receiving the medical device data further comprises receiving a signal that one of the medical devices has data available for uploading. In addition, the medical device may be a home sleep testing device or a flow generator used for respiratory therapy.

A generated diagnostic report may contain statistical indications which assist diagnosis and provide an area where a healthcare professional may input their clinical interpretation. The diagnostic report may also include a prescription for therapy that identifies one or more therapy devices and one or more therapeutic settings to be used by a patient. The diagnostic report for therapy may be displayed as HTML on a web browser or as a Portable Document Format (PDF).

The method may also include assigning a therapy provider to a patient that is ready for therapy; transferring diagnostic information for the patient to the assigned therapy provider; and electronically importing therapy settings from the diagnostic information onto the therapy device to be used by the patient.

In another aspect, an apparatus for integrated electronic management of diagnostic and therapy data of a plurality of sleep disorder breathing patients may include: a memory configured to store medical data, and one or more processors in communication with the memory. The one or more processors may be configured to receive medical device data for a plurality of medical device users; associate the received medical device data with a corresponding patient records; determine whether received medical device data is diagnostic or usage data; update the patient records in accordance with the determination of whether the received medical device data is diagnostic or usage data; store a list of therapy providers within a system of therapy providers; receive a request to display the list from a diagnostic provider; receive diagnostic data from the plurality of medical devices; generate summary statistics by processing the diagnostic data using a set of predetermined analysis criteria; receive a request generated by a clinical user; and transmit, in response to the request, a diagnostic report comprising the summary statistics.

The processors may also be configured to store a list of medical devices and accessory items; receive a request to display the list by a clinical user; receive clinical settings information generated by the clinical user; receive text generated by the clinical user; transmit a prescription for therapy report displaying a selected item manifest and clinical settings; securely allow access to diagnostic and prescription data of a patient record by the selected therapy provider; dynamically update the therapy provider's available patient list with at least one patient record; display the additional patient record in the patient list; securely display patient information, diagnostic reports and prescription for therapy reports as selected by a therapy provider user; receive a request to assign a patient with a therapy device ID that corresponds to the prescription; and automatically transfer clinical settings information into the memory from the prescription.

3 BRIEF DESCRIPTION OF THE DRAWINGS

The present technology is illustrated by way of example, and not by way of limitation, in the figures of the accompanying drawings, in which like reference numerals refer to similar elements including:

3.1 Therapy Systems

FIG. 1A shows a system in accordance with the present technology. A patient 1000 wearing a patient interface 3000, in the form of nasal pillows, receives a supply of air at positive pressure from a RPT device 4000. Air from the RPT device is humidified in a humidifier 5000, and passes along an air circuit 4170 to the patient 1000.

3.2 Therapy

3.2.1 Respiratory system

Figure 2A:
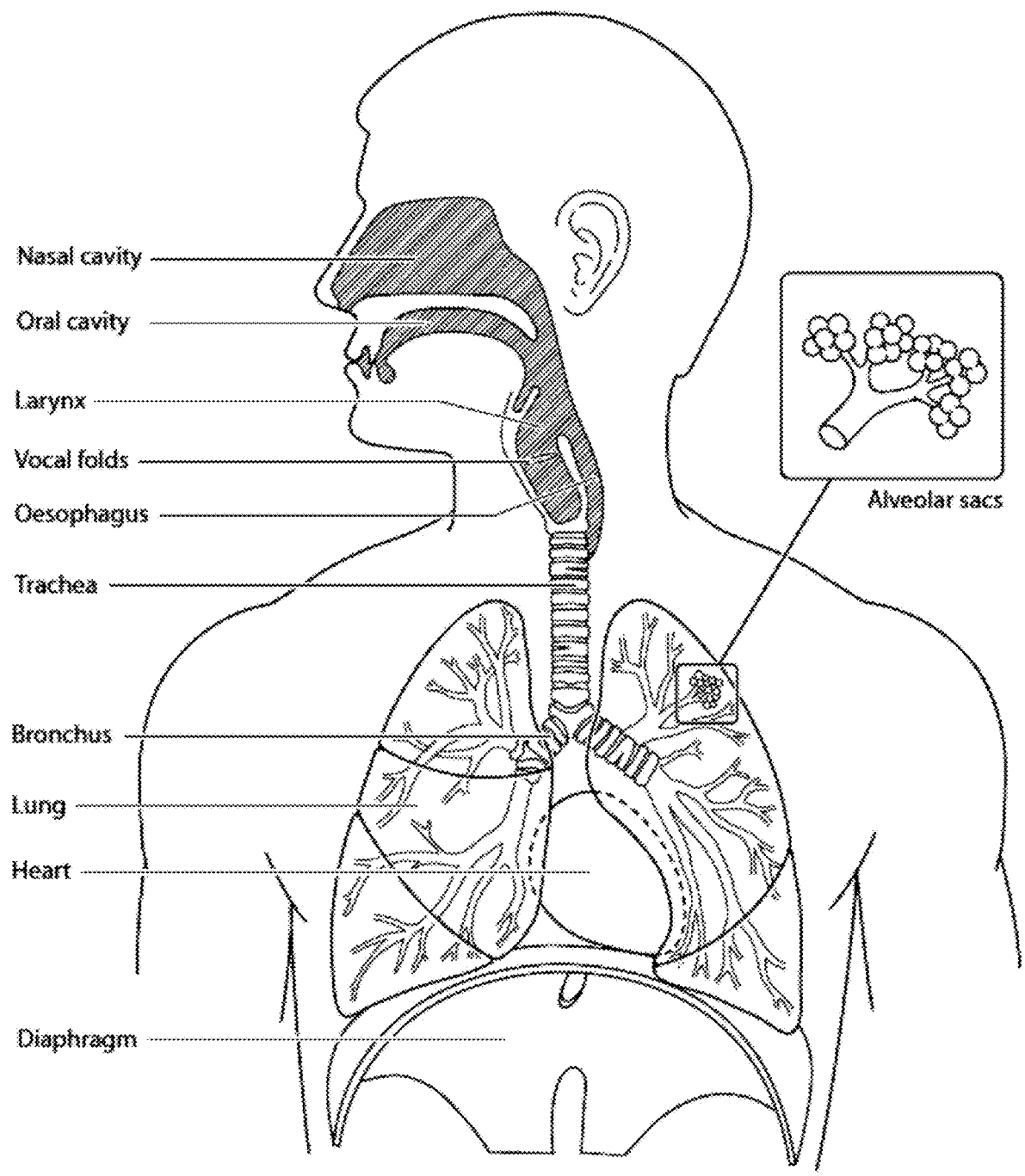

FIG. 2A shows an overview of a human respiratory system including the nasal and oral cavities, the larynx, vocal folds, oesophagus, trachea, bronchus, lung, alveolar sacs, heart and diaphragm.

Figure 2B:
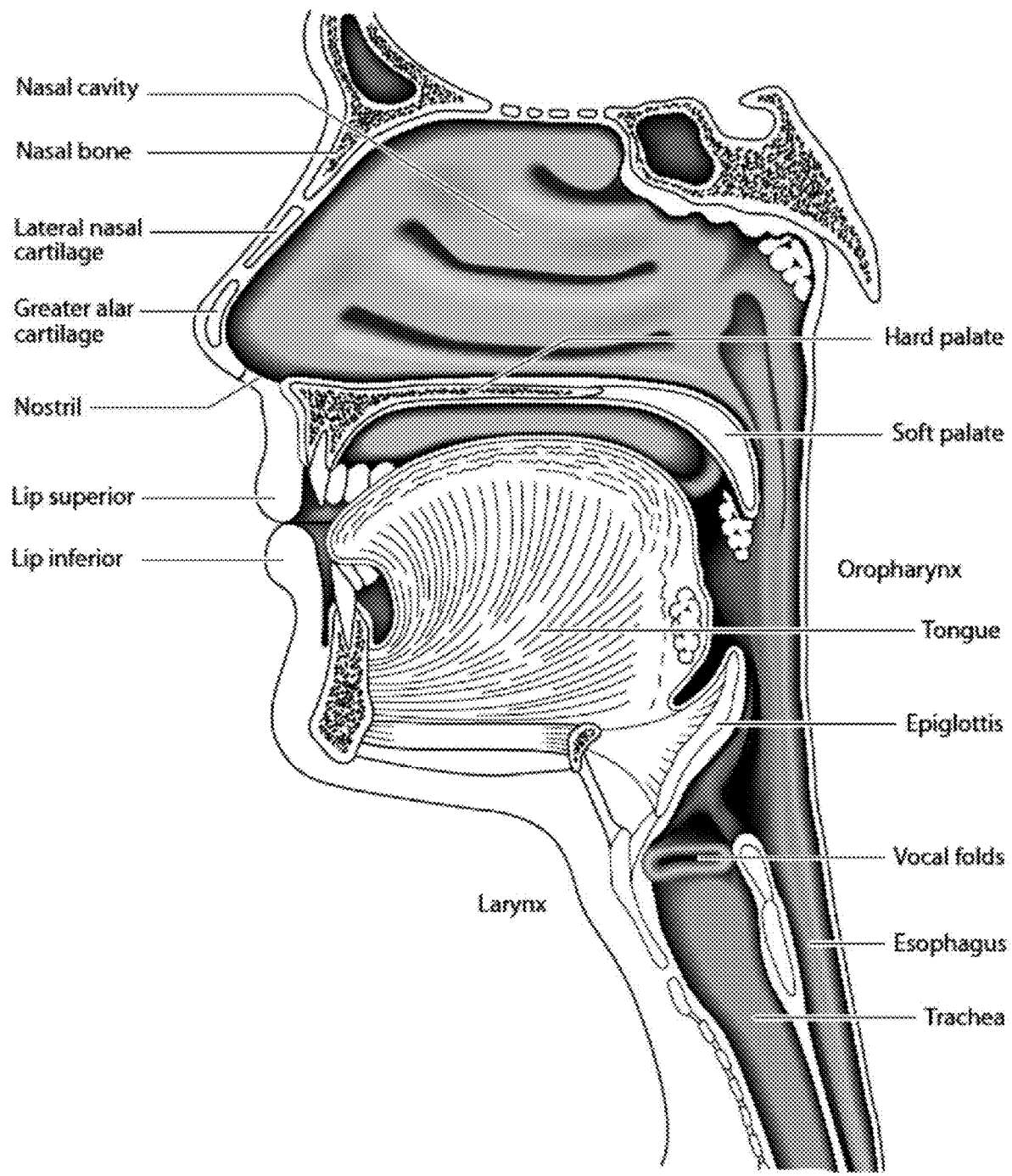

FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

3.2.2 Facial Anatomy

Figure 2C:
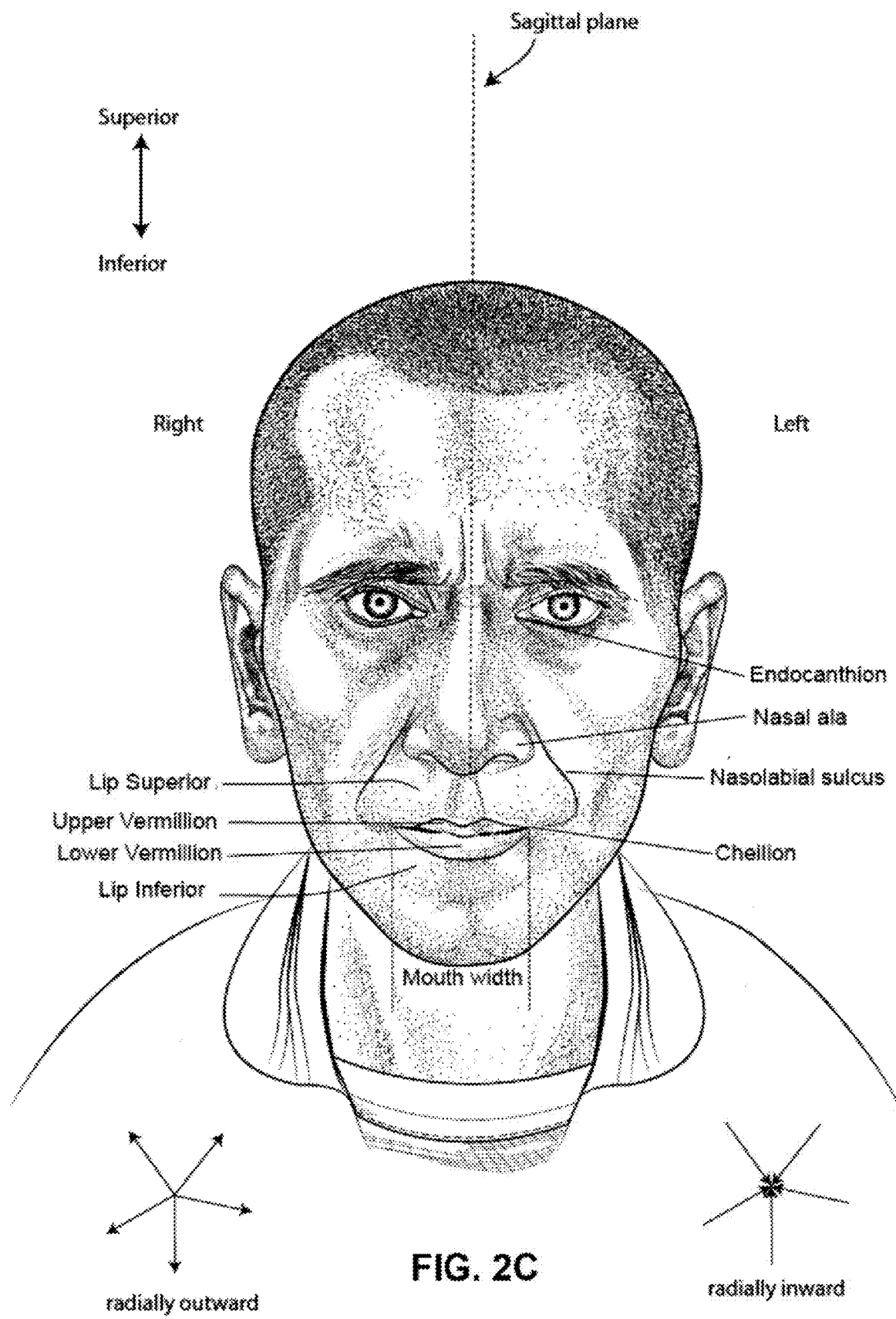

FIG. 2C is a front view of a face with several features of surface anatomy identified including the lip superior, upper vermillion, lower vermillion, lip inferior, mouth width, endocanthion, a nasal ala, nasolabial sulcus and cheilion.

3.3 Patient Interface

Figure 3A:
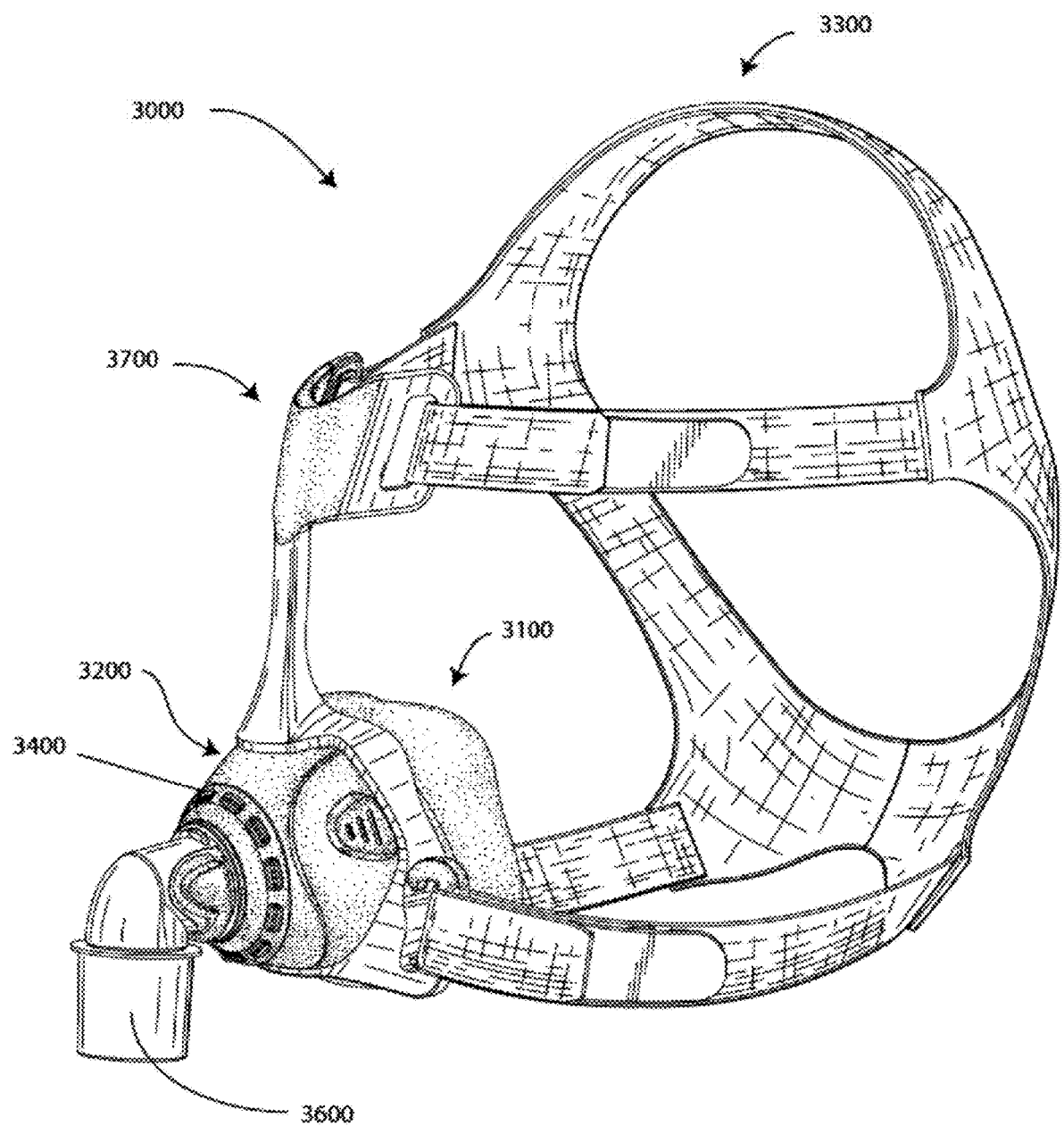

FIG. 3*a* shows an example of a patient interface known in the prior art.

3.4 Respiratory Pressure Therapy (RPT) Device

Figure 4A:
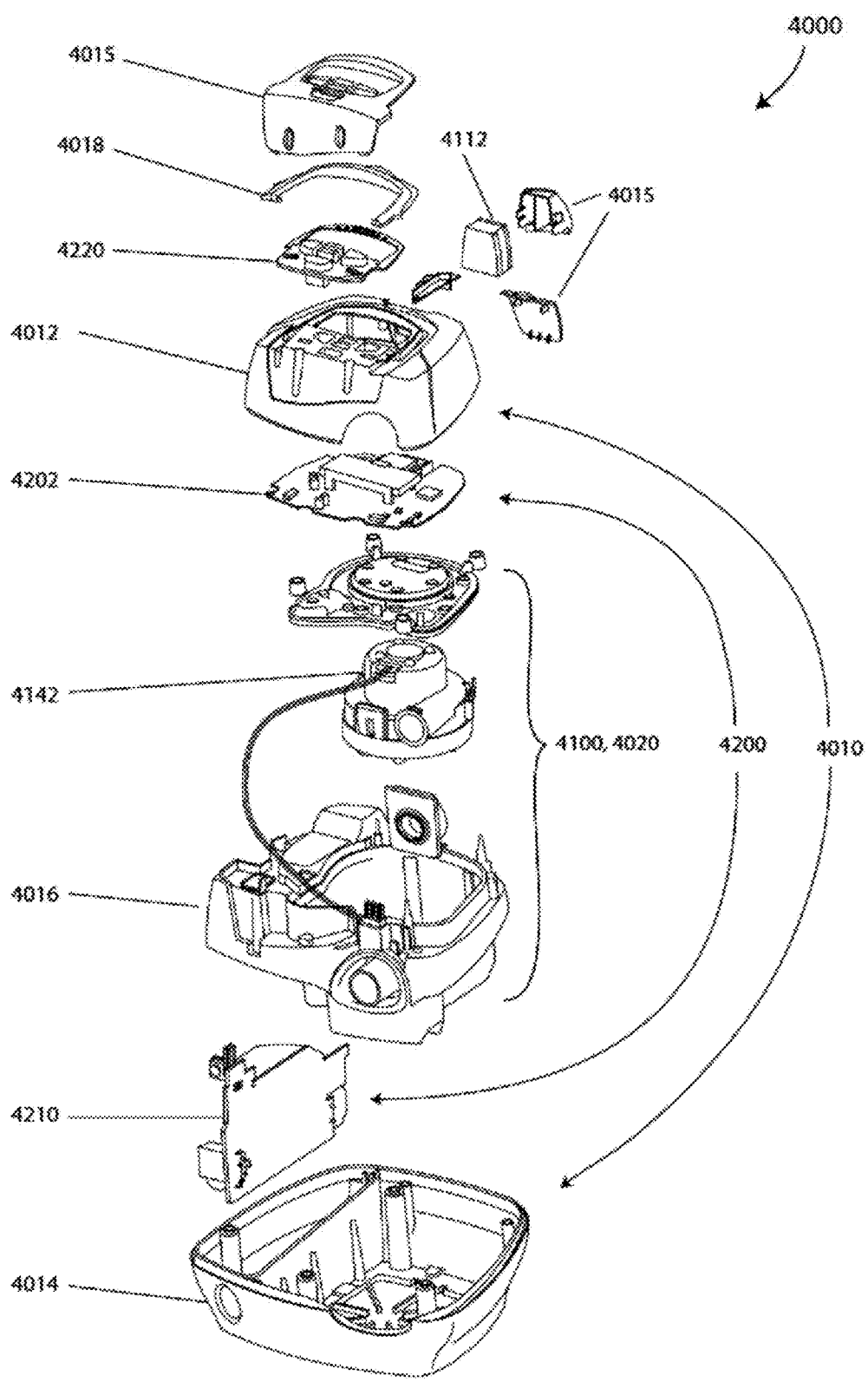

FIG. 4A shows a RPT device in accordance with one form of the present technology.

Figure 4B:
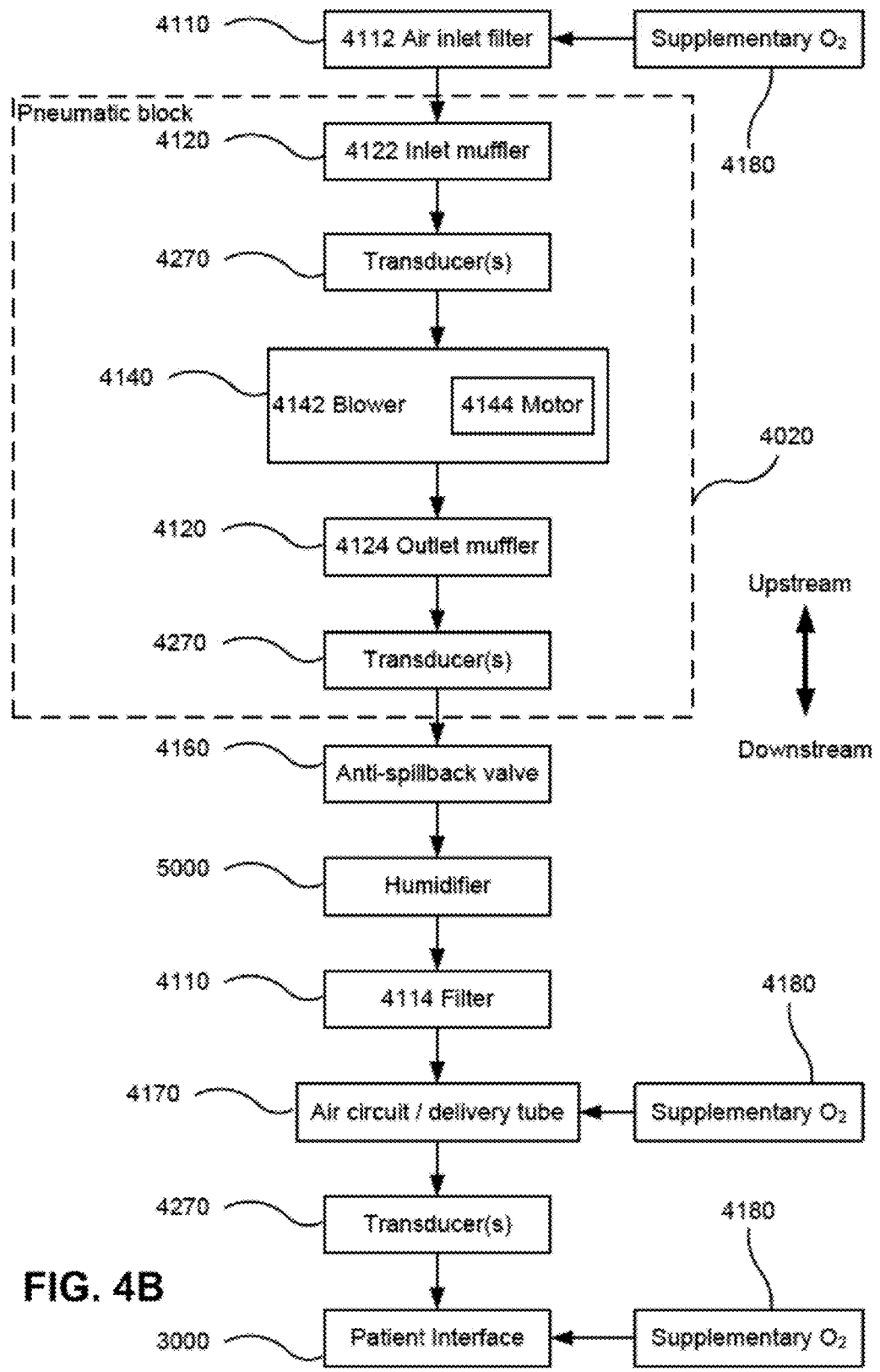

FIG. 4B shows a schematic diagram of the pneumatic circuit of a RPT device in accordance with one form of the present technology. The directions of upstream and downstream are indicated.

Figure 4C:
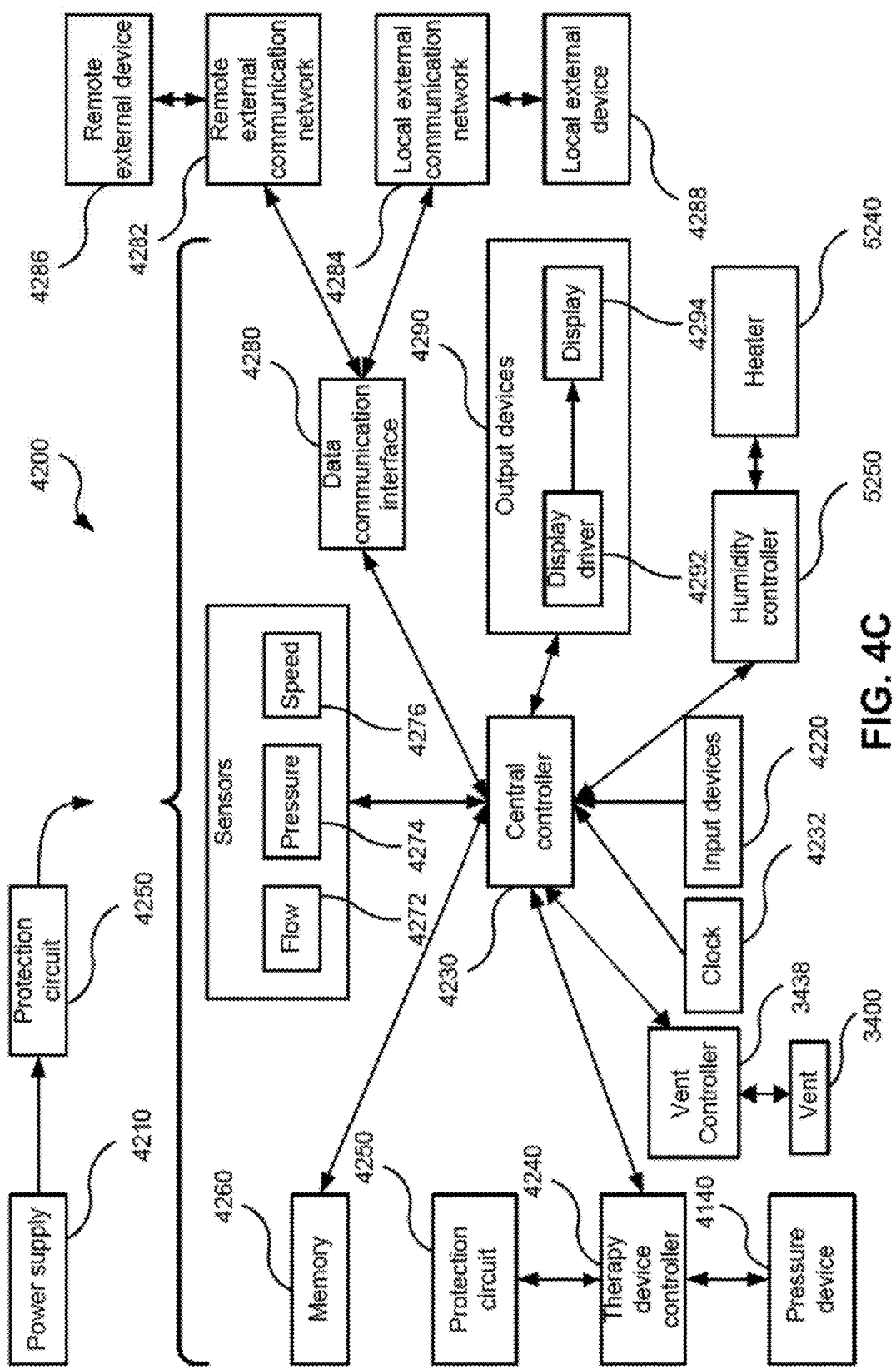

FIG. 4C shows a schematic diagram of the electrical components of a RPT device in accordance with one aspect of the present technology.

3.5 Humidifier

Figure 5A:
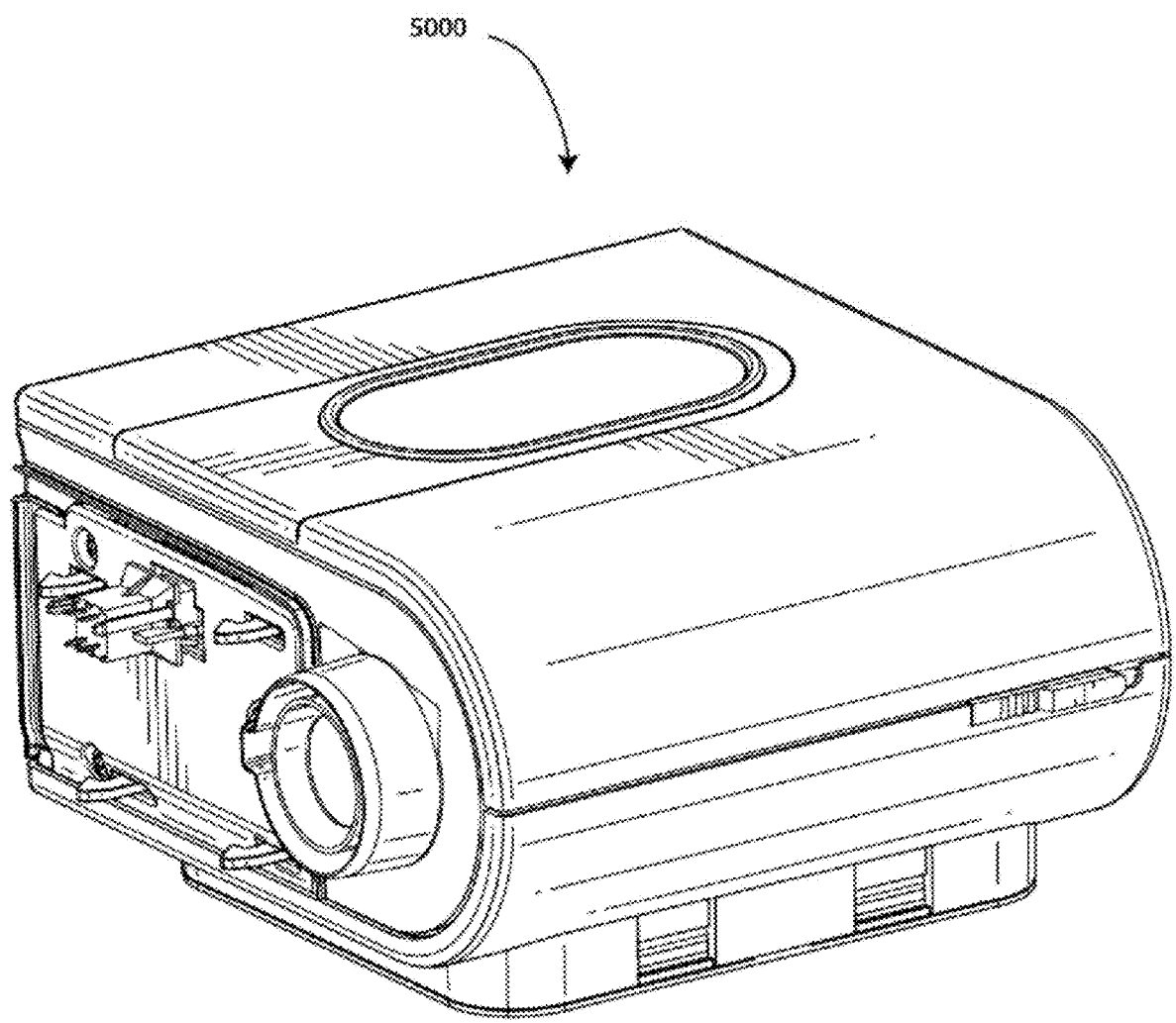

FIG. 5A shows a humidifier in accordance with one aspect of the present technology.

3.6 Breathing Waveforms

Figure 6A:
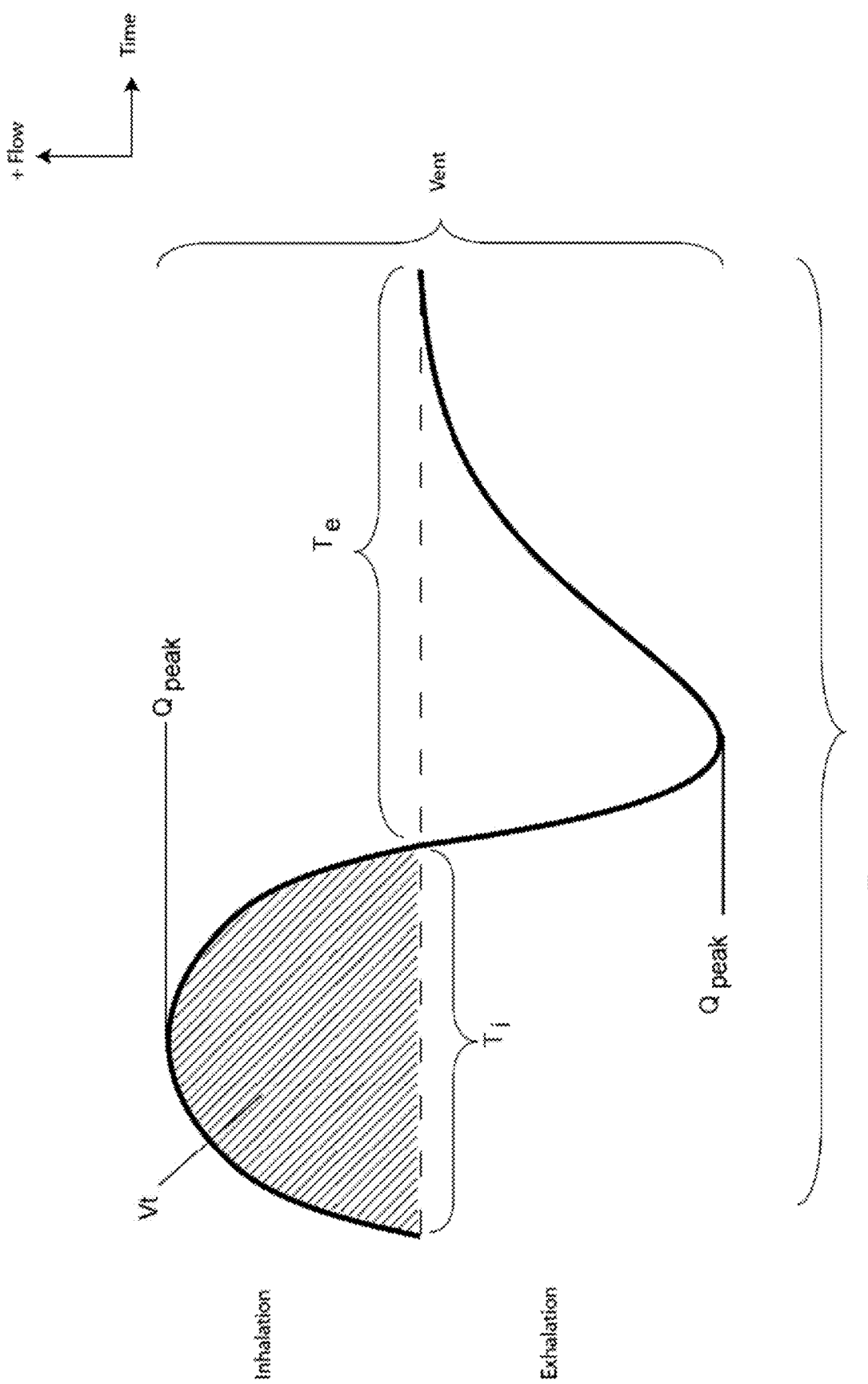

FIG. 6A shows a model typical breath waveform of a person while sleeping, the horizontal axis is time, and the vertical axis is respiratory flow. While the parameter values may vary, a typical breath may have the following approximate values: tidal volume, Vt, 0.5 L, inhalation time, Ti, 1.6 s, peak inspiratory flow, Qpeak, 0.4 L/s, exhalation time, Te, 2.4 s, peak expiratory flow, Qpeak, −0.5 L/s. The total duration of the breath, Ttot, is about 4 s. The person typically breathes at a rate of about 15 breaths per minute (BPM), with Ventilation, Vent, about 7.5 L/s. A typical duty cycle, the ratio of Ti to Ttot is about 40%.

3.7 Diagnosis and Therapy Data Management

Figure 7:
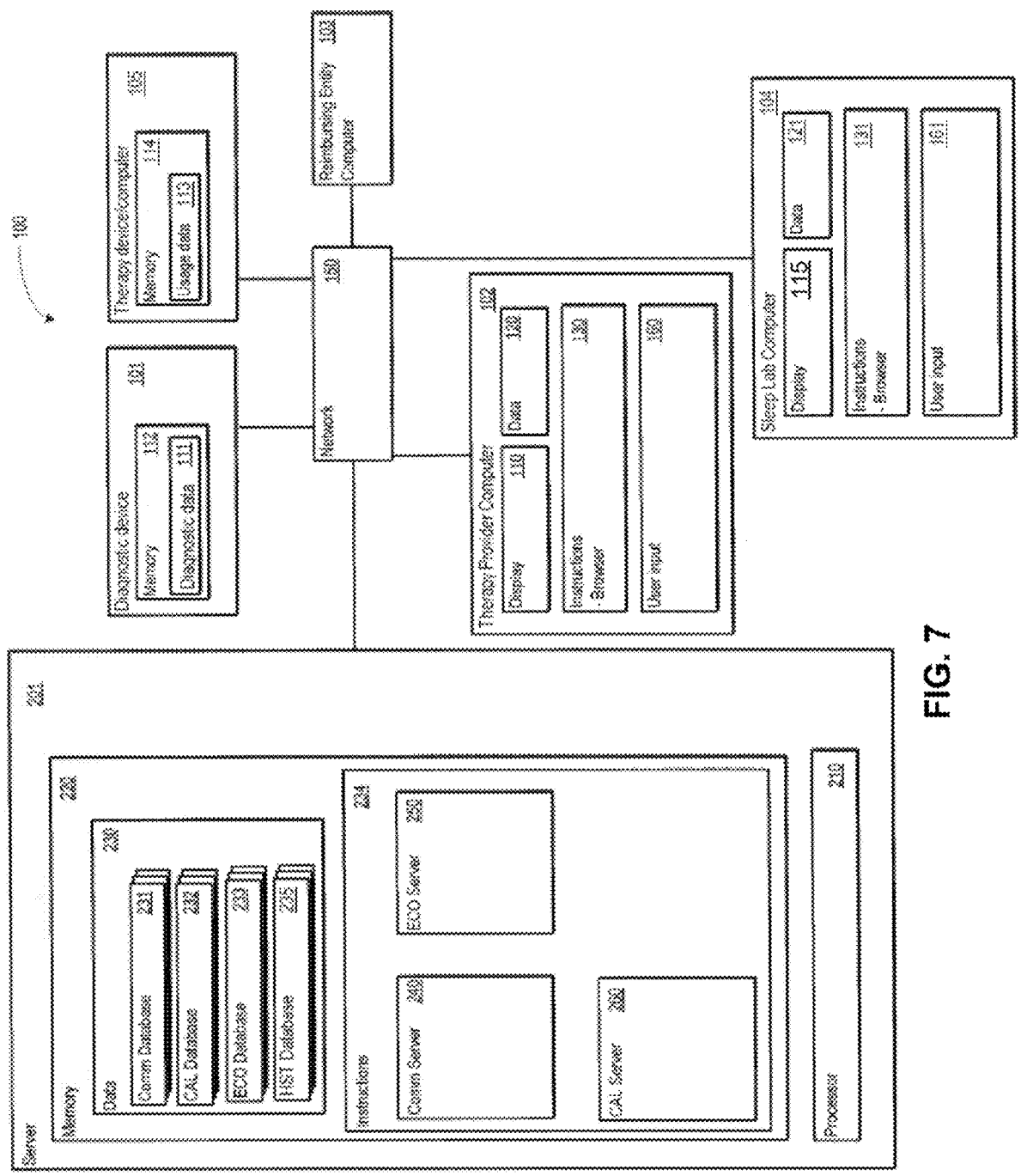
Figure 8:
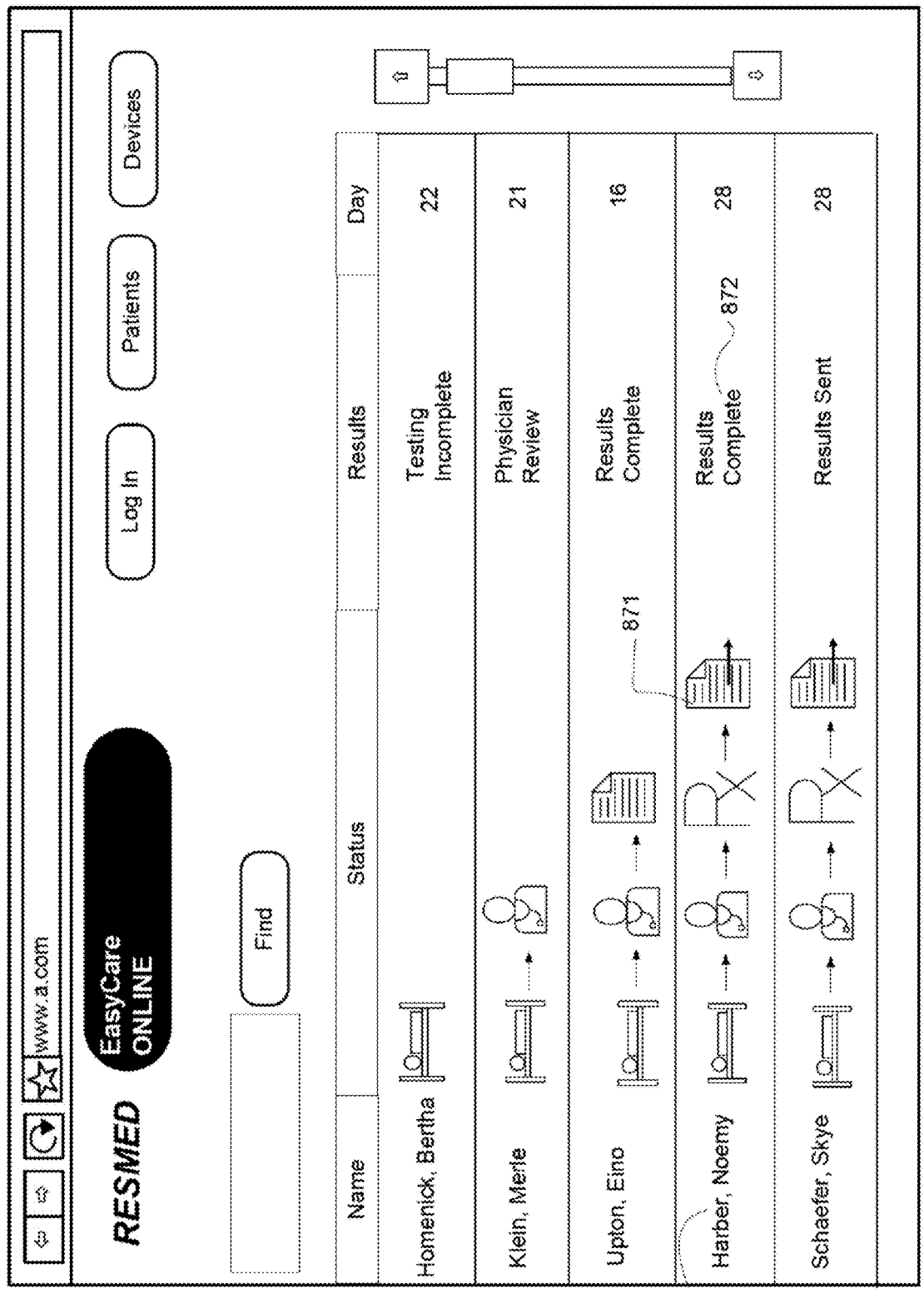

FIG. 7 shows a system 100 that may be used in diagnosing and treating a patient's sleep disorder breathing.

FIGS. 8-14 are various webpages that may be displayed in accordance with aspects of the disclosed system.

Figure 15:
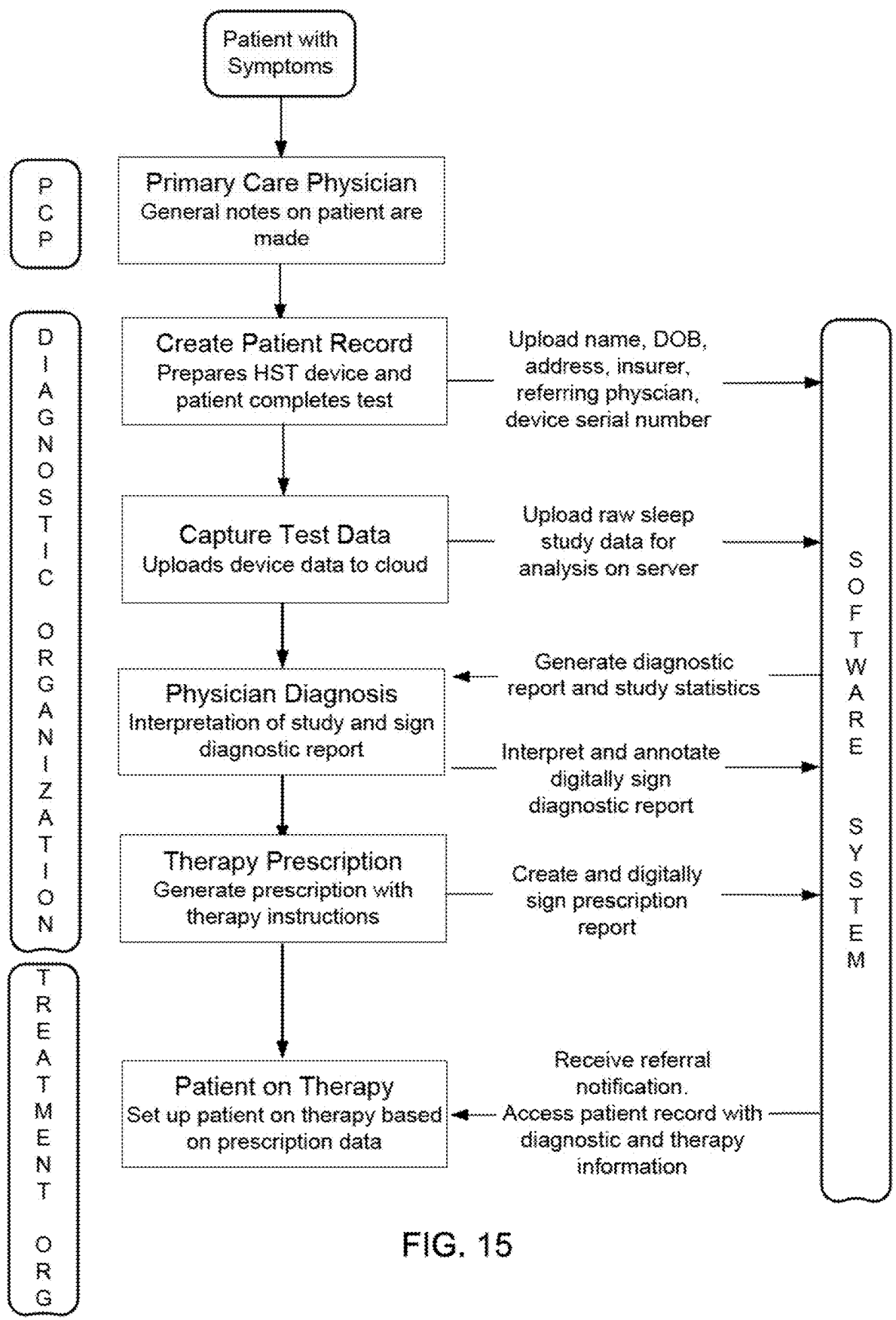

FIG. 15 is a schematic diagram of aspect of the disclosed system and methods.

4 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

4.1 Therapy Systems

In one form, the present system comprises an apparatus for treating a respiratory disorder. The apparatus may comprise a flow generator or blower for supplying pressurised respiratory gas, such as air, to the patient 1000 via an air delivery tube leading to a patient interface 3000.

4.2 Therapy

In one form, the present technology comprises a method for treating a respiratory disorder comprising the step of applying positive pressure to the entrance of the airways of a patient 1000.

4.2.1 Nasal CPAP for OSA

In one form, the present technology comprises a method of treating Obstructive Sleep Apnea in a patient by applying nasal continuous positive airway pressure to the patient.

4.3 Patient Interface 3000

A non-invasive patient interface 3000 in accordance with one aspect of the present technology comprises the following functional aspects: a seal-forming structure 3100, a plenum chamber 3200, a positioning and stabilising structure 3300, a vent 3400 and a connection port 3600 for connection to air circuit 4170. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

4.3.1 Seal-Forming Structure 3100

In one form of the present technology, a seal-forming structure 3100 provides a sealing-forming surface, and may additionally provide a cushioning function.

A seal-forming structure 3100 in accordance with the present technology may be constructed from a soft, flexible, resilient material such as silicone.

In one form, the seal-forming structure 3100 comprises a sealing flange and a support flange. Preferably the sealing flange comprises a relatively thin member with a thickness of less than about 1 mm, for example about 0.25 mm to about 0.45 mm, that extends around the perimeter 3210 of the plenum chamber 3200. Support flange may be relatively thicker than the sealing flange. The support flange is disposed between the sealing flange and the marginal edge of the plenum chamber 3200, and extends at least part of the way around the perimeter 3210. The support flange is or includes a spring-like element and functions to support the sealing flange from buckling in use. In use the sealing flange can readily respond to system pressure in the plenum chamber 3200 acting on its underside to urge it into tight sealing engagement with the face.

In one form the seal-forming portion of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose; a stalk, a flexible region on the underside of the cone and connecting the cone to the stalk. In addition, the structure to which the nasal pillow of the present technology is connected includes a flexible region adjacent the base of the stalk. The flexible regions can act in concert to facilitate a universal joint structure that is accommodating of relative movement—both displacement and angular—of the frusto-cone and the structure to which the nasal pillow is connected. For example, the frusto-cone may be axially displaced towards the structure to which the stalk is connected.

In one form the non-invasive patient interface 3000 comprises a seal-forming portion that forms a seal in use on an upper lip region (that is, the lip superior) of the patient's face.

In one form the non-invasive patient interface 3000 comprises a seal-forming portion that forms a seal in use on a chin-region of the patient's face.

4.3.2 Plenum Chamber 3200

Preferably the plenum chamber 3200 has a perimeter 3210 that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. Preferably the seal-forming structure 3100 extends in use about the entire perimeter 3210 of the plenum chamber 3200.

Figure 1A:
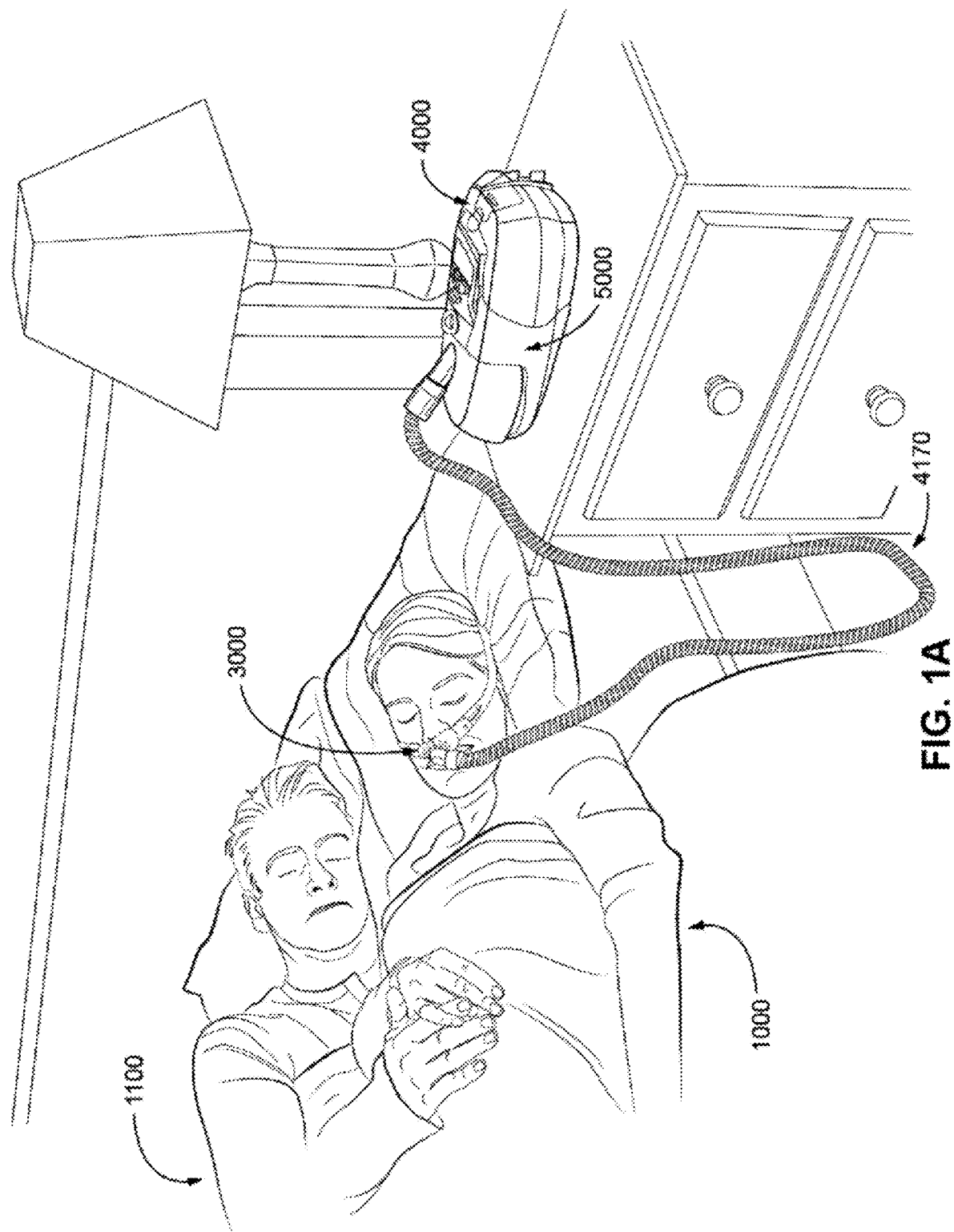
FIG. 1B shows a system including a patient 1000 wearing a patient interface 3000, in the form of a nasal mask, receives a supply of air at positive pressure from a RPT device 4000. Air from the RPT device is humidified in a humidifier 5000, and passes along an air circuit 4170 to the patient 1000.
FIG. 1C shows a system including a patient 1000 wearing a patient interface 3000, in the form of a full-face mask, receives a supply of air at positive pressure from a RPT device. Air from the RPT device is humidified in a humidifier 5000, and passes along an air circuit 4170 to the patient 1000.
Figure 1B:
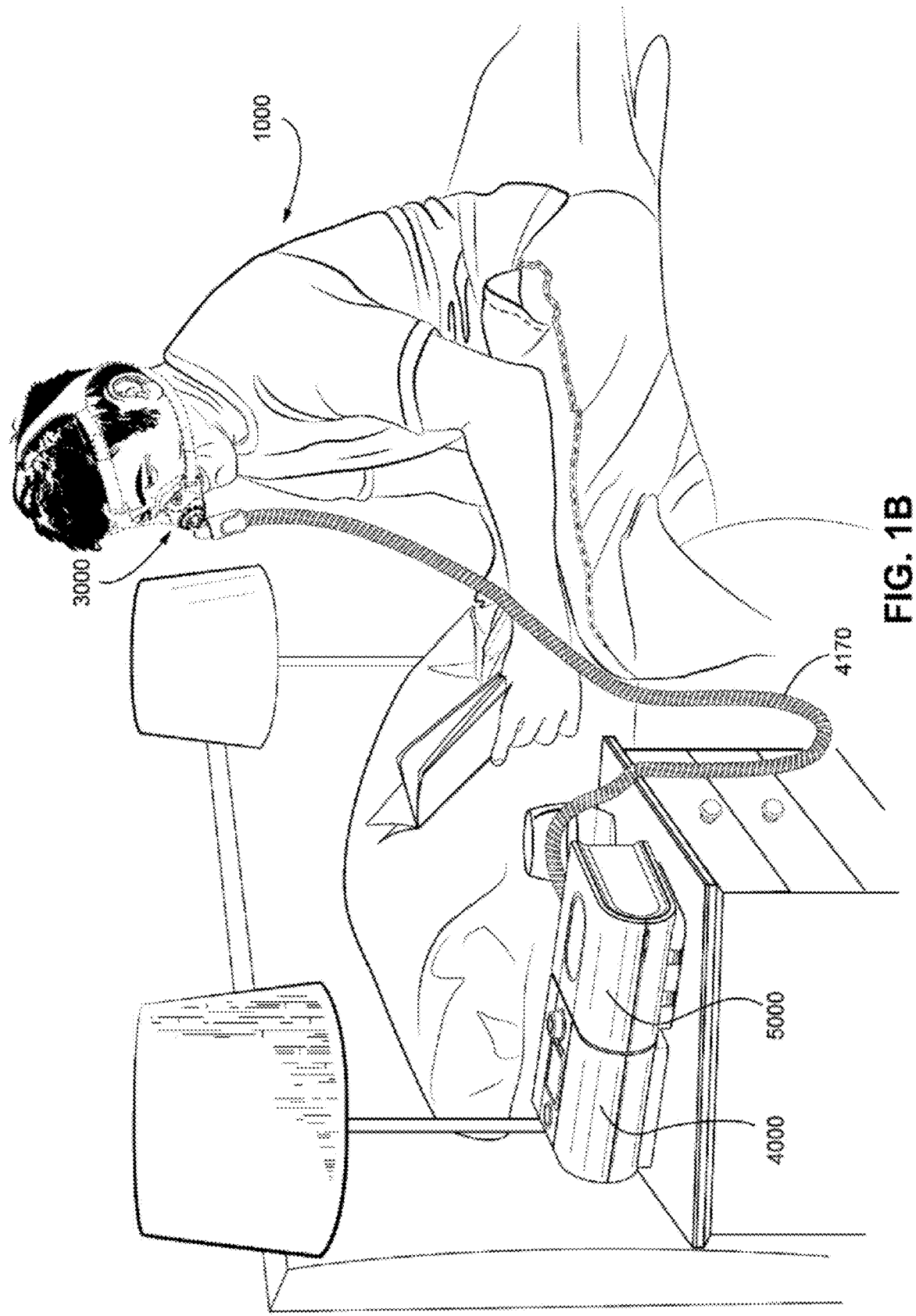
Figure 1C:

In one form, the plenum chamber 3200 may surround and/or be in fluid communication with the nares of the patient where the plenum chamber 3200 is a part of a nasal mask (e.g. shown in FIG. 1b). In another form, the plenum chamber 3200 may surround and/or be in fluid communication with the nares and the mouth of the patient where the plenum chamber 3200 is a part of a full-face mask (e.g., shown in FIG. 1C). In yet another form, the plenum chamber 3200 may engage and/or be in fluid communication with one or more of the nares of the patient where the plenum chamber 3200 is a part of nasal pillows.

4.3.3 Positioning and Stabilising Structure 3300

Preferably the seal-forming structure 3100 of the patient interface 3000 of the present technology is held in sealing position in use by the positioning and stabilising structure 3300.

4.4 RPT Device 4000

An example RPT device 4000 that may be suitable for implementing aspects of the present technology may include mechanical and pneumatic components 4100, electrical components 4200 and may be programmed to execute one or more of the control methodologies or algorithms described throughout this specification. The RPT device may have an external housing 4010, preferably formed in two parts, an upper portion 4012 of the external housing 4010, and a lower portion 4014 of the external housing 4010. In alternative forms, the external housing 4010 may include one or more panel(s) 4015. Preferably the RPT device 4000 comprises a chassis 4016 that supports one or more internal components of the RPT device 4000. In one form a pneumatic block 4020 is supported by, or formed as part of the chassis 4016. The RPT device 4000 may include a handle 4018.

The pneumatic path of the RPT device 4000 preferably comprises an inlet air filter 4112, an inlet muffler 4122, a controllable pressure device 4140 capable of supplying air at positive pressure (preferably a blower 4142), and an outlet muffler 4124. One or more flow sensors 4272 and pressure sensors 4274 are included in the pneumatic path.

The preferred pneumatic block 4020 comprises a portion of the pneumatic path that is located within the external housing 4010.

The RPT device 4000 preferably has an electrical power supply 4210, one or more input devices 4220, a central controller 4230, a therapy device controller 4240 and/or any of the controllers previously described, a pressure device 4140, one or more protection circuits 4250, memory 4260, transducers (also referred to as sensors) 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

The central controller 4230 of the RPT device 4000, which may include one or more processors, can be programmed to execute one or more algorithm modules, preferably including a pre-processing module, a therapy engine module, a pressure control module, and further preferably a fault condition module. It may further include a vent control module that may be configured with one or more of the vent control methodologies described throughout this specification.

4.4.1 RPT Device Mechanical & Pneumatic Components 4100

4.4.1.1 Air Filter(s) 4110

A RPT device in accordance with one form of the present technology may include an air filter 4110, or a plurality of air filters 4110.

In one form, an inlet air filter 4112 is located at the beginning of the pneumatic path upstream of a blower 4142. See FIG. 4B.

In one form, an outlet air filter 4114, for example an antibacterial filter, is located between an outlet of the pneumatic block 4020 and a patient interface 3000. See FIG. 4B.

4.4.1.2 Muffler(s) 4120

In one form of the present technology, an inlet muffler 4122 is located in the pneumatic path upstream of a blower 4142. See FIG. 4B.

In one form of the present technology, an outlet muffler 4124 is located in the pneumatic path between the blower 4142 and a patient interface 3000. See FIG. 4B.

4.4.1.3 Pressure Device 4140

In a preferred form of the present technology, a pressure device 4140 for producing a flow of air at positive pressure is a controllable blower 4142. For example the blower may include a brushless DC motor 4144 with one or more impellers housed in a volute. The blower may be preferably capable of delivering a supply of air, for example about 120 litres/minute, at a positive pressure in a range from about 4 cmH$_2$O to about 20 cmH$_2$O, or in other forms up to about 30 cmH$_2$O.

The pressure device 4140 is under the control of the therapy device controller 4240.

4.4.1.4 Transducer(s) 4270

In one form of the present technology, one or more transducers 4270 are located upstream of the pressure device 4140. The one or more transducers 4270 are constructed and arranged to measure properties of the air at that point in the pneumatic path.

In one form of the present technology, one or more transducers 4270 are located downstream of the pressure device 4140, and upstream of the air circuit 4170. The one or more transducers 4270 are constructed and arranged to measure properties of the air at that point in the pneumatic path.

In one form of the present technology, one or more transducers 4270 are located proximate to the patient interface 3000.

4.4.1.5 Anti-Spill Back Valve 4160

In one form of the present technology, an anti-spill back valve is located between the humidifier 5000 and the pneumatic block 4020. The anti-spill back valve is constructed and arranged to reduce the risk that water will flow upstream from the humidifier 5000, for example to the motor 4144.

4.4.1.6 Air Circuit 4170

An air circuit 4170 in accordance with an aspect of the present technology is constructed and arranged to allow a flow of air or breathable gasses between the pneumatic block 4020 and the patient interface 3000.

4.4.1.7 Oxygen Delivery

In one form of the present technology, supplemental oxygen 4180 is delivered to a point in the pneumatic path.

In one form of the present technology, supplemental oxygen 4180 is delivered upstream of the pneumatic block 4020.

In one form of the present technology, supplemental oxygen 4180 is delivered to the air circuit 4170.

In one form of the present technology, supplemental oxygen 4180 is delivered to the patient interface 3000.

4.4.2 RPT Device Electrical Components 4200

4.4.2.1 Power Supply 4210

In one form of the present technology, power supply 4210 is internal of the external housing 4010 of the RPT device 4000. In another form of the present technology, power supply 4210 is external of the external housing 4010 of the RPT device 4000.

In one form of the present technology, power supply 4210 provides electrical power to the RPT device 4000 only. In another form of the present technology, power supply 4210 provides electrical power to both RPT device 4000 and humidifier 5000. The power supply may also optionally provide power to any actuator, controller and/or sensors for a vent arrangement as described throughout this specification

4.4.2.2 Input Devices 4220

In one form of the present technology, a RPT device 4000 includes one or more input devices 4220 in the form of buttons, switches or dials to allow a person to interact with the device. These may be implemented for entering settings for operation of the components of the RPT device such as the vent arrangement. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form the input device 4220 may be constructed and arranged to allow a person to select a value and/or a menu option.

4.4.2.3 Central Controller 4230

In one form of the present technology, the central controller 4230 is a dedicated electronic circuit configured to receive input signal(s) from the input device 4220, and to provide output signal(s) to the output device 4290 and/or the therapy device controller 4240.

In one form, the central controller 4230 is an application-specific integrated circuit. In another form, the central controller 4230 comprises discrete electronic components.

In another form of the present technology, the central controller 4230 is a processor suitable to control a RPT device 4000 such as an x86 INTEL processor.

A processor of a central controller 4230 suitable to control a RPT device 4000 in accordance with another form of the present technology includes a processor based on ARM Cortex-M processor from ARM Holdings. For example, an STM32 series microcontroller from ST MICROELECTRONICS may be used.

Another processor suitable to control a RPT device 4000 in accordance with a further alternative form of the present technology includes a member selected from the family ARMS-based 32-bit RISC CPUs. For example, an STR9 series microcontroller from ST MICROELECTRONICS may be used.

In certain alternative forms of the present technology, a 16-bit RISC CPU may be used as the processor for the RPT device 4000. For example a processor from the MSP430 family of microcontrollers, manufactured by TEXAS INSTRUMENTS, may be used.

The processor is configured to receive input signal(s) from one or more transducers 4270, and one or more input devices 4220.

The processor is configured to provide output signal(s) to one or more of an output device 4290, a therapy device controller 4240, a data communication interface 4280 and humidifier controller 5250.

In some forms of the present technology, the processor of the central controller 4230, or multiple such processors, is configured to implement the one or more methodologies described herein such as the one or more algorithms 4300 expressed as computer programs stored in a non-transitory computer readable storage medium, such as memory 4260. In some cases, as previously discussed, such processor(s) may be integrated with a RPT device 4000. However, in some forms of the present technology the processor(s) may be implemented discretely from the flow generation components of the RPT device 4000, such as for purpose of performing any of the methodologies described herein without directly controlling delivery of a respiratory therapy. For example, such a processor may perform any of the methodologies described herein for purposes of determining control settings for a ventilator or other respiratory related events by analysis of stored data such as from any of the sensors described herein. Similarly, such a processor may perform any of the methodologies described herein for purposes controlling operation of any vent arrangement described in this specification.

4.4.2.4 Clock 4232

Preferably RPT device 4000 includes a clock 4232 that is connected to processor.

4.4.2.5 Therapy Device Controller 4240

In one form of the present technology, therapy device controller 4240 is a pressure control module 4330 that forms part of the algorithms 4300 executed by the processor of the central controller 4230.

In one form of the present technology, therapy device controller 4240 is a dedicated motor control integrated circuit. For example, in one form a MC33035 brushless DC motor controller, manufactured by ONSEMI is used.

4.4.2.6 Protection Circuits 4250

Preferably a RPT device 4000 in accordance with the present technology comprises one or more protection circuits 4250.

One form of protection circuit 4250 in accordance with the present technology is an electrical protection circuit.

One form of protection circuit 4250 in accordance with the present technology is a temperature or pressure safety circuit.

4.4.2.7 Memory 4260

In accordance with one form of the present technology the RPT device 4000 includes memory 4260, preferably non-volatile memory. In some forms, memory 4260 may include battery powered static RAM. In some forms, memory 4260 may include volatile RAM.

Preferably memory 4260 is located on PCBA 4202. Memory 4260 may be in the form of EEPROM, or NAND flash.

Additionally or alternatively, RPT device 4000 includes removable form of memory 4260, for example a memory card made in accordance with the Secure Digital (SD) standard.

In one form of the present technology, the memory 4260 acts as a non-transitory computer readable storage medium on which is stored computer program instructions expressing the one or more methodologies described herein, such as the one or more algorithms 4300.

4.4.2.8 Transducers 4270

Transducers may be internal of the device, or external of the RPT device. External transducers may be located for example on or form part of the air delivery circuit, e.g. the patient interface. External transducers may be in the form of non-contact sensors such as a Doppler radar movement sensor that transmit or transfer data to the RPT device.

4.4.2.8.1 Flow

A flow sensor 4272 in accordance with the present technology may be based on a differential pressure transducer, for example, an SDP600 Series differential pressure transducer from SENSIRION. The differential pressure transducer is in fluid communication with the pneumatic circuit, with one of each of the pressure transducers connected to respective first and second points in a flow restricting element.

In use, a signal representing total flow Qt from the flow sensor 4272 is received by the processor.

4.4.2.8.2 Pressure

A pressure transducer 4274 in accordance with the present technology is located in fluid communication with the pneumatic circuit. An example of a suitable pressure transducer is a sensor from the HONEYWELL ASDX series. An alternative suitable pressure transducer is a sensor from the NPA Series from GENERAL ELECTRIC.

In use, a signal from the pressure transducer 4274 is received by the central controller processor. In one form, the signal from the pressure transducer 4274 is filtered prior to being received by the central controller 4230.

4.4.2.8.3 Motor Speed

In one form of the present technology a motor speed signal is generated. A motor speed signal is preferably provided by therapy device controller 4240. Motor speed may, for example, be generated by a speed sensor 4276, such as a Hall effect sensor.

4.4.2.9 Data Communication Interface 4280

In one preferred form of the present technology, a data communication interface 4280 is provided, and is connected to central controller processor. Data communication interface 4280 is preferably connectable to remote external communication network 4282. Data communication interface 4280 is preferably connectable to local external communication network 4284. Preferably remote external communication network 4282 is connectable to remote external device 4286. Preferably local external communication network 4284 is connectable to local external device 4288.

In one form, data communication interface 4280 is part of processor of central controller 4230. In another form, data communication interface 4280 is an integrated circuit that is separate from the central controller processor.

In one form, remote external communication network 4282 is the Internet. The data communication interface 4280 may use wired communication (e.g. via Ethernet, or optical fibre) or a wireless protocol to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such remote external device 4286 may be accessible to an appropriately authorised person such as a clinician.

Preferably local external device 4288 is a personal computer, mobile phone, tablet or remote control.

4.4.2.10 Output Devices Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

4.4.2.10.1 Display Driver 4292

A display driver 4292 receives as an input the characters, symbols, or images intended for display on the display 4294 and converts them to commands that cause the display 4294 to display those characters, symbols, or images.

4.4.2.10.2 Display 4294

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

4.5 Communication and Data Management System

FIG. 7 depicts an example system 100 in which aspects of the disclosure may be implemented. This example should not be considered as limiting the scope of the disclosure or usefulness of the features described herein. The system is compatible with, and processes data from, both diagnostic and therapy devices. As provided above, patient medical diagnostic device 101 may be any sleep testing device used in connection with diagnosis of the patient's sleep-related breathing disorder. Therapy device 105 may be any device used in connection with providing therapy for the patient's sleep-related breathing disorder. The diagnostic device 101 and therapy device 105 may each include the RPT device 4000, humidifier 5000, and patient interface 3000 described herein. Thus, when receiving data from a medical device, the system may be configured to not only associate the received medical device data with a corresponding patient record, but also determine whether the received medical device data is diagnostic usage data or therapy usage data and update the patient records accordingly, based on predetermined one or more criteria. The data identification may be associated with the data itself or with a device ID from which it is received. If the medical device data is determined as diagnostic data, the system may be configured to process the diagnostic data and to generate a diagnostic report and/or a prescription based on predetermined analysis criteria. The system may be further configured to display the diagnostic report and/or the prescription to a diagnostic provider for review and to enable an electronic transfer of a diagnosis report or a therapy prescription, based on the diagnostic data, to a therapy provider.

System 100 has the ability to seamlessly transfer a patient's health information (including demographic and medical data) directly from diagnosis through to patient therapy within the same system within a single patient record. To facilitate this workflow, system 100 may have the following functional features:

The ability to upload and analyse therapy management data within the same software system as the diagnostic data, allowing for a single software system for both diagnostic and therapy management users. This may be helpful in avoiding formatting problems when transitioning between different software applications.

The ability to share the patient's diagnostic record with therapy management users, thus enabling them to save a patient's therapy and compliance data directly to the common patient record having the patient's diagnostic report and prescription data.

The ability of therapy provider to access the diagnostic data, as well as therapy settings information from the initial prescription data, as saved in the patient's record, or even for the therapy device to be automatically configured via a cable connection, wireless connection, or a memory card, by accessing this record.

As the patient uses medical diagnostic device 101, diagnostic data 111 may be recorded on a storage medium, also referred to as memory, 112. Diagnostic data 111 may include any data relating to the patient's sleep test, such as date, time and duration of test, as well as physiological data obtained during the test, such as recorded respiratory flow data, respiratory effort data, oximetry and pulse data, or other clinical information. Memory 112 may be of any non-transitory type capable of storing information accessible by a processor, including a computer-readable medium, or other medium that stores data that may be read with the aid of an electronic device, such as a hard-drive, memory card, ROM, RAM, DVD or other optical disks, as well as other write-capable and read-only memories.

Server 201 includes a processor 210 and a memory 220 for storing data 230 and instructions 234. Memory 220 stores information accessible by processor 210, including instructions 234 that may be executed or otherwise used by the processor 21. The memory 220 may be of any non-transitory type capable of storing information accessible by the processor, including a computer-readable medium, or other medium that stores data that may be read with the aid of an electronic device, such as a hard-drive, memory card, ROM, RAM, DVD or other optical disks, as well as other write-capable and read-only memories. Systems and methods may include different combinations of the foregoing, whereby different portions of the instructions and data are stored on different types of media.

The instructions 234 may be any set of instructions to be executed directly (such as machine code) or indirectly (such as scripts) by the processor. For example, the instructions may be stored as computer code on the computer-readable medium. In that regard, the terms "instructions" and "programs" may be used interchangeably herein. The instructions may be stored in object code format for direct processing by the processor, or in any other computer language including scripts or collections of independent source code modules that are interpreted on demand or compiled in advance. Functions, methods and routines of the instructions are explained in more detail below. Instructions 234 may also contain instructions for operating one or more virtual servers, such as Communication (Comm) server 240, Easy Care Online (ECO) Server 250, and Communication Abstraction Layer (CAL) server 260.

The Communications Server (Comm) is responsible for communicating with wireless Therapy Devices and validating their output. The Communications Server's core responsibilities may include, communicating with Flow Generators via a Communication Module or inbuilt Communications Device; validating the incoming wireless data; and converting the wireless data into a format which can be read by the CAL server.

The CAL server is responsible for communicating with Therapy Devices. The CAL server's core responsibilities may include, obtaining daily summary data for active patients; retrieving and changing therapy device settings; and converting raw therapy device data into an easily digestible format.

The ECO Server is responsible for application functionality within the system. The ECO Server's core responsibilities includes, presenting patient and device information within the user interface, and writing and managing patient health information; and running application related processes.

The data 230 may be retrieved, stored or modified by processor 210 in accordance with the instructions 234. For instance, although the system and method is not limited by any particular data structure, the data may be stored in computer registers, in a relational database as a table having a plurality of different fields and records, XML documents or flat files. The data may also be formatted in any computer-readable format. The data may comprise any information useful in identifying the relevant information, such as numbers, descriptive text, proprietary codes, references to data stored in other areas of the same memory or different memories (including other locations accessible through other network connections) or information that is used by a function to calculate the relevant data. Data 230 may include one or more databases, including a Comm database 231, CAL database 232, ECO database 233, and HST database 235. Various types of data may be saved in these databases. For example, the Comm database 231, CAL database 232 and the ECO database 233 may store data associated with the respective servers, as described above. The HST database may store diagnostic data received from diagnostic devices 101.

The processor 210 may be any conventional processor, including commercially available processors. Alternatively, the processor may be a dedicated device such as an ASIC or FPGA. Although FIG. 2 functionally illustrates the processor, memory, and other elements of server 201 as being within the same block, it will be understood by those of ordinary skill in the art that the processor and memory may actually comprise multiple processors and memories that may or may not be stored within the same physical housing. For example, memory may be a hard drive or other storage media located in a housing different from that of server 201. Accordingly, references to a processor or computer will be understood to include references to a collection of processors or computers or memories that may or may not operate in parallel or even be located at the same site. Rather than using a single processor to perform the steps described herein some of the components such as steering components and deceleration components may each have their own processor that only performs calculations related to the component's specific function. Thus, server 201 may be referred to as both a system and an apparatus.

Computers 102, 103 and 104 may include all of the components normally used in connection with a computer, such as a central processing unit (CPU), memory (e.g., RAM and internal hard drives) for storing data 120 and 121 and instructions 130 and 131 (e.g. a web browser for displaying webpages in HTML and a portable document format (PDF) reader), an electronic display 110 and 115 (e.g., a monitor having a screen, a small LCD touch-screen or any other electrical device that is operable to display information), and user input 160 and 161 (e.g., a mouse, keyboard, touch screen, and/or microphone).

The memory 112 may be internal to diagnostic device 101 which may be accessed by connecting an USB data cable to a separate computer. Accordingly, the term "medical device" in such a case may be interpreted broadly to include a personal computer, such as a desktop or mobile computer, which contains usage data, including diagnostic data 111 collected from a medical device, such as a home sleep testing device. In addition, while FIG. 2 illustrates server 201 and computers 101-104 as being connected via a network 150, each two or more devices within system 100 may be connected via a separate network or via the Internet.

In one example, any one of the ECO server 250 and its associated ECO database 233, the Comm server 240 and its associated Comm database 231 and the CAL server 260 and its associated CAL database 232 may reside on a device at a location that is remote from the remaining servers. In addition, at least two of these servers, such as the Comm server 240, Comm database 231, CAL server 260, and CAL database 232, may exist on a single device.

4.6 Example Methods

In order for a patient to undergo a test, the patient may need to be issued with a diagnostic order by the patient's treating physician. The patient is referred to a sleep test where the patient may be issued a diagnostic device 101 for sleep testing. The diagnostic device 101 may collect any one of the following types of data Polysomnography (PSG) data, polygraphy data, oximetry data, pneumatic or Respiratory Inductance Plethysmography (RIP)-based respiratory effort data, respiratory flow data, audio signal data, body position data etc.

The patient's record is first created during the diagnostic stage, when the patient is approved for running a diagnostic test. The patient's record may comprise any data that is associated with the patient or with the patient's condition, such as the patient's personal details (name, gender, age, address, contact details etc.), symptoms, treating physician, insurance provider, type of insurance cover etc. From diagnostic provider's computer 104, where the patient's record is created, it is transferred to the ECO database of server 201. It should be appreciated that computer 104 may not be a personal computer, but an administration computer used at the diagnostic provider clinic. As such, this computer may be operated, at least partially, not by the specific diagnostic physician responsible for the testing and diagnosis of the respective patient, but by a data administrator on the site. For example, it can be envisaged that such an administrator may be responsible for creating the patient's record.

During the actual test, the diagnostic device collects diagnostic data indicating any respiratory condition that the patient may have, as well as other information, such as the type and model of the diagnostic device, the patient's details, including these of the referring diagnostic physician, time and dates of usage etc.

During the actual test, the diagnostic device saves the diagnostic test data 111 in memory 112. A user of system 100, such as a user of diagnostic provider computer 104, may have a remote access to the memory 112 of the medical diagnostic device 101. Alternatively, user of diagnostic provider computer 104 may extract the portable memory card of device 101 and download the data to computer 104. An addition, one can connect the device 101, e.g. via a USB cable, to the diagnostic provider computer 104 to access the device memory 112. A web browser 131 on the diagnostic provider computer 104 may then be used to contact server 201 and upload diagnostic data 111 to one or more of the databases 231, 232, 233 and 235.

The diagnostic data 111 provided to server 201 from diagnostic device 101 may be stored in a CAL database 232, which may identify the type of patient device from which it came. For example, each diagnostic device 101 may be assigned a device ID, which is provided to server 201 along with the diagnostic data. The diagnostic data may then be stored by server 201 in a database that uses the device ID to associate the received data with the appropriate patient diagnostic device 101. The usage data from therapy device 105 may be processed in a similar manner In some instances, a patient is required to use a medical diagnostic device for a set duration and exhibit certain clinical symptoms in order to be eligible to qualify for therapy of the patient's sleep disorder breathing. For example, a patient who has been ordered a home sleep test may be required to use the diagnostic device for at least four hours and exhibit an Apnea-Hypopnea Index (AHI) of greater than 5 in order for a physician to write a prescription for CPAP therapy. The prescription (also referred to as prescription data or prescription information) may be saved in the HST database 235). System 100 may be used to track whether the patient has been compliant in using the diagnostic device and may assist a physician in making a diagnosis.

Once the patient is tested, a diagnosis may be issued by the sleep provider and may be based on the diagnostic information produced by system 100, and more specifically by the testing/diagnostic device 101. Depending on the patient's diagnosis, a diagnostic provider, and more specifically a diagnostic physician, may issue a prescription for therapy. The diagnostic provider may input his or her clinical interpretation of diagnostic data into the patient's record. In addition, the ECO database may contain a list of clinical options for a number of therapy devices 105 which the diagnostic physician may assign to a patient, as they see appropriate. In assigning these devices, ECO server 250 may select the appropriate pre-set of settings from the ECO database and then allow the diagnostic provider to input the clinical values into the appropriate fields. The data corresponding to the patient and device type may then be stored on server 201, such as in the ECO database 233.

In some cases, the testing compliance criteria is usually defined by the reimbursing authority and may be set in the system 100 by a user, such as the sleep physician or clinician in the diagnostic site (a user of diagnostic computer 104). For example, usage data from diagnostic device 101 may demonstrate that a patient was tested for at least 4 hours and had an Obstructive Sleep Apnea with an AHI of 20, and therefore may be a candidate for CPAP therapy. A qualified healthcare professional, such as a sleep physician, may use computer 104 to write a prescription within a web browser 131 for therapy for a CPAP device at a pressure of 14 cmH20. Diagnostic computer 104 may transmit the prescription data to server 201, wherein it will be stored in a database, such as in the ECO database 233, to become a part of the patient's record.

Patients prescribed for therapy will need to open new records with their diagnostic provider, e.g. on diagnostic computer 104. Instead, the proposed system allows access to their record, including any usage and settings data, to a therapy provider computer 102 so that the patients can be supplied and set up with a therapy device. For example, the patient diagnosed with Obstructive Sleep Apnea will need to have their patient information and prescription sent to an assigned therapy provider who can supply them with a CPAP device. System 100 may be used to facilitate the assignment, access, and transfer of data from the diagnostic provider to a trusted therapy provider. Instead of creating a new patient record, the patient's record may be electronically transferred. Furthermore, instead of transferring the patient record, the system may allow the therapy provider to access the present patient record, as created and updated during the diagnostic stage. Depending on the arrangement, the therapy provider may be allowed access either to the entire patient record, or only to some of the patient identification data, diagnostic data, diagnostic report, therapy prescription and initial device setting data. Also, the access to the respective data may be open access with full functionality, or only limited access. Such a limited access, for example, may involve the capability to view and/or download the diagnostic data, but not to modify it.

The therapy provider may be allowed to modify the access of the diagnostic provider. For example, after the record is made accessible to the therapy provider, the therapy provider may allow continuous access by the diagnostic provider to the patient's record. Depending on the arrangement, the diagnostic provider may be allowed access either to the entire patient record, or only to some of the patient data, such as the patient's identification data, diagnostic data, but not to the patient's therapy data. Also, the access to the respective data may be open access with full functionality, or only limited access. Such a limited access, for example, may involve the capability to view and/or download the therapy data, but not to modify it.

Thus, once the electronic patient record is created, medical practitioners associated with either the diagnostic stage or the therapy stage may be provided various level of access to the electronic patient record during both the diagnostic stage and the therapy stage.

A health care professional at a diagnostic provider location may monitor the status of their patient's diagnostics data and forward their prescription to a therapy provider by contacting server 201 via a website accessed on diagnostic computer 104. For example, the healthcare professional may access patient data via webpage 800 (the 'dashboard') shown in FIG. 8. Webpage 800 may contain a list of active patients who are currently proceeding through home sleep testing, including status indicators that indicate the status of the patient's diagnostic tests. The various icons indicate the different status of the patient. For example—the bed-like icons indicate that the patient is still in testing phase. The physician profile-like icon indicates that the patient has moved to the diagnostic report phase. Different colour, for example, may be used to indicate whether the report has or has not being issued yet. Similarly, the Rx icon indicates that the patient's diagnostic report is ready and the patient has moved to the prescription stage. Again, different colour may be used to indicate whether the prescription has or has not being issued yet. Finally, icon 871 may indicate that the patient is in the "patient record being finalised" phase.

Figure 9:
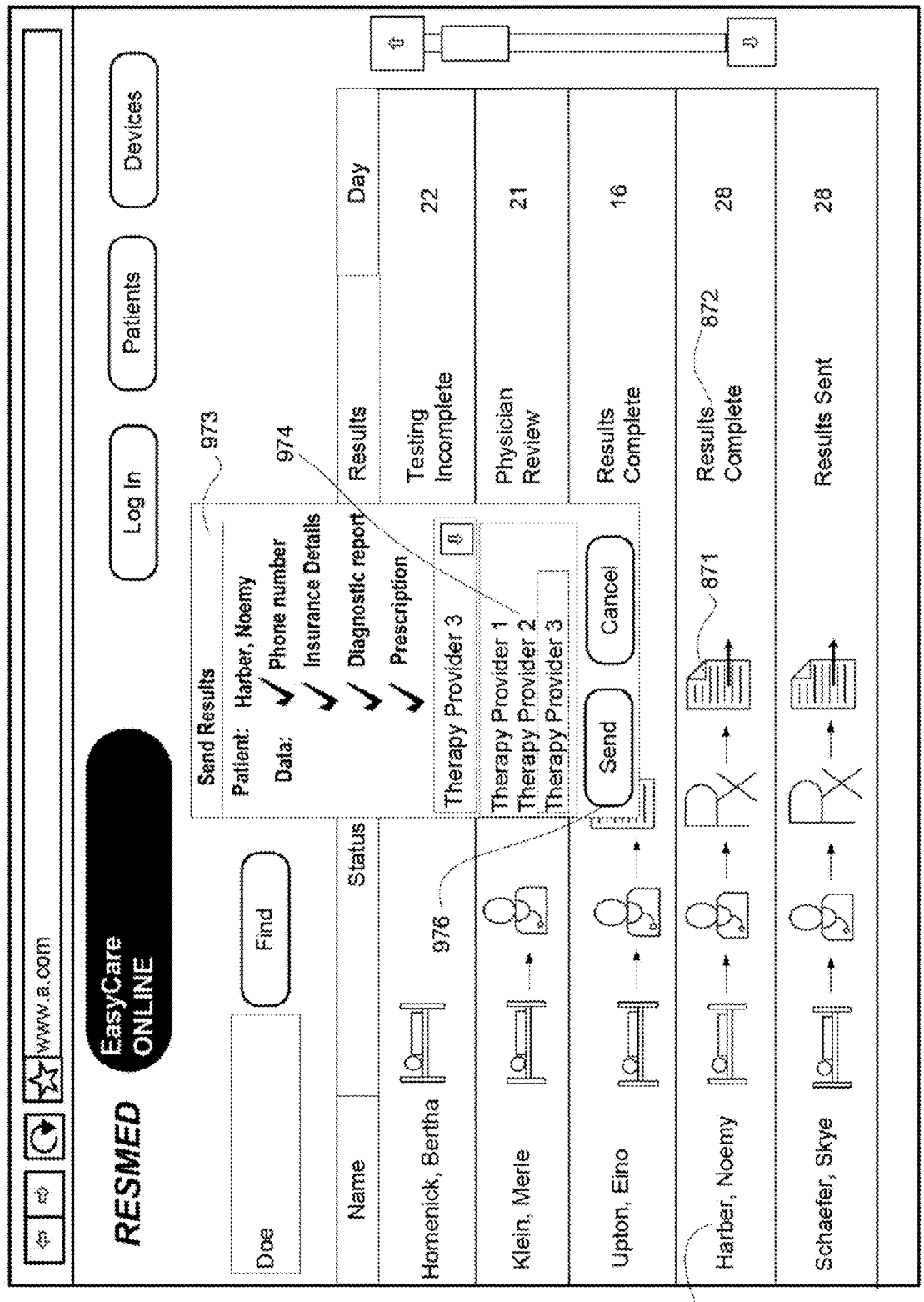

As shown in FIG. 9, the patient Noemy Harber has completed her testing, diagnostic report and prescriptions stages. The icon Rx indicates that Noemy's diagnostic report and prescription are ready. As indicated by status indicator 872, the patient's record has undergone even the final checks and is now ready to be sent. Such final checks may involve verification of the patient's name, phone number and insurance provider details.

Once a diagnostic provider associated with diagnostic computer 104 has determined that the patient needs to go onto therapy, the diagnostic provider may click on the icon 871. As shown in FIG. 9, pop-up window 973 may appear when icon 871 is selected. Pop-up window 973 may then be used to send patient information to a selected therapy provider that is to be associated with the therapy of the patient. The diagnostic provider may select a particular therapy provider from a list of therapy providers using drop-down menu 974. For that purpose, the diagnostic provider computer 104 may send a transmission to the ECO server requesting data for available therapy providers within the system of therapy providers. ECO server will then provide data responsive to the request, which will populate menu 974 within the web browser 131. By clicking on send button 976 the healthcare professional can instantly confirm their choice and initiate a command to the ECO server to transfer ownership of the patient record to the therapy provider nominated in menu 974. Clicking on send button 976 transfers ownership of the patient to the therapy provider and changes the status of the patient within the dashboard to "Results Sent." In this way, healthcare professionals may quickly and easily transfer their patients directly into the therapy provider's inbox without having to manually transfer paper records via fax, mail or via the patient.

In some instances, ECO server 250 may automatically provide therapy provider computer 102, by way of web browser (e.g. instructions 130) and via the network 150, with the usage and therapy settings data required to set up a patient on therapy device 105 as directed by the diagnostic provider physician's prescription. For example, a therapy provider may be notified by the ECO server 250 when a diagnosis and prescription for therapy has been created on the server by a diagnostics provider and assigned to them. This allows the therapy provider to be immediately informed of a patient's transfer into their care and ensures that a patient is supplied with the correct therapy device having the required therapeutic settings. The settings data can be automatically transferred directly to therapy device 105, such as via an internet connection, or manually inputted via an SD card or the therapy device's interface.

Figure 11:
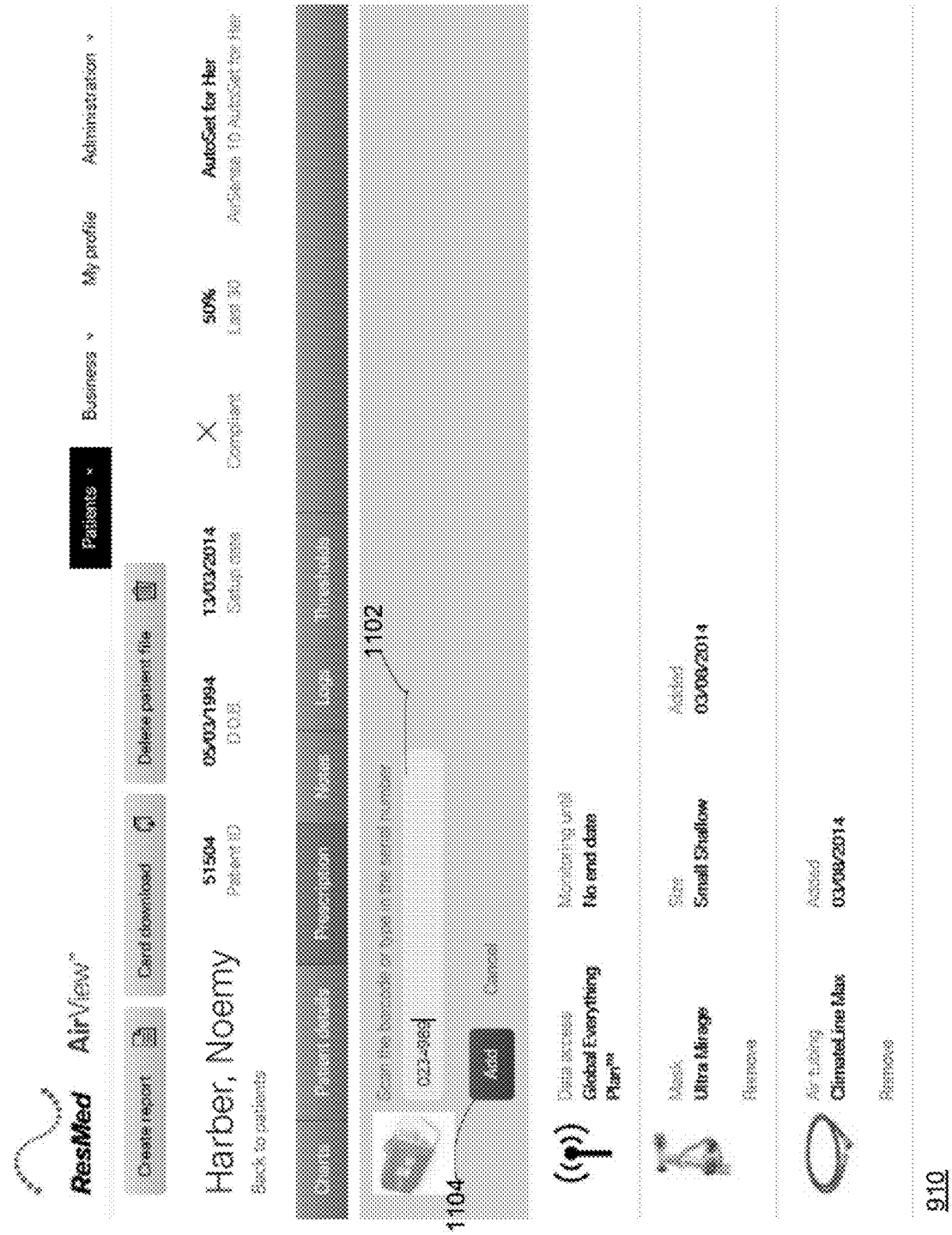

A therapy provider may be automatically alerted that a patient has been referred to them by messaging service, such as E-mail or SMS messaging, or by contacting therapy provider computer 102 via server 201. For example, the therapy provider or an administrator at the therapy provider's office may access the transferred patient information described above via webpage 900 shown in FIG. 10. Webpage 900 may contain various data items, such as patient names 970, referring diagnostic providers 982, contact details 983, diagnostic and prescription information 984, insurer data 986, an acceptance status 987, or any other patient information of interest. A therapy provider may use webpage 900 to accept or reject a patient referral. For example, the therapy provider may select a patient having an "accept/reject" status, and then designate the patient's referral as either "accepted" or "rejected." Once the therapy provider has accepted the desired patient, the therapy provider computer 102 may send a transmission to the ECO server requesting additional patient health information from the ECO database for the relevant patient ID. ECO server will then provide patient demographic and therapy settings data responsive to the request, which once available will be used to pre-populate data fields required for a setup of the new patient with a therapy device. Thus, the system is configured to dynamically update the therapy provider's available patient list the record of the new patient, as well as to start displaying the additional patient record in the patient list of the therapy provider. For example, FIG. 11 shows webpage 910 in which the patient Noemy Harber may be automatically assigned various therapy devices in accordance with her prescription. The healthcare professional may alter the assigned devices or identify additional therapy devices or components in field 1102 and have those devices or components assigned to the patient by selecting the Add icon 1104.

Figure 10:
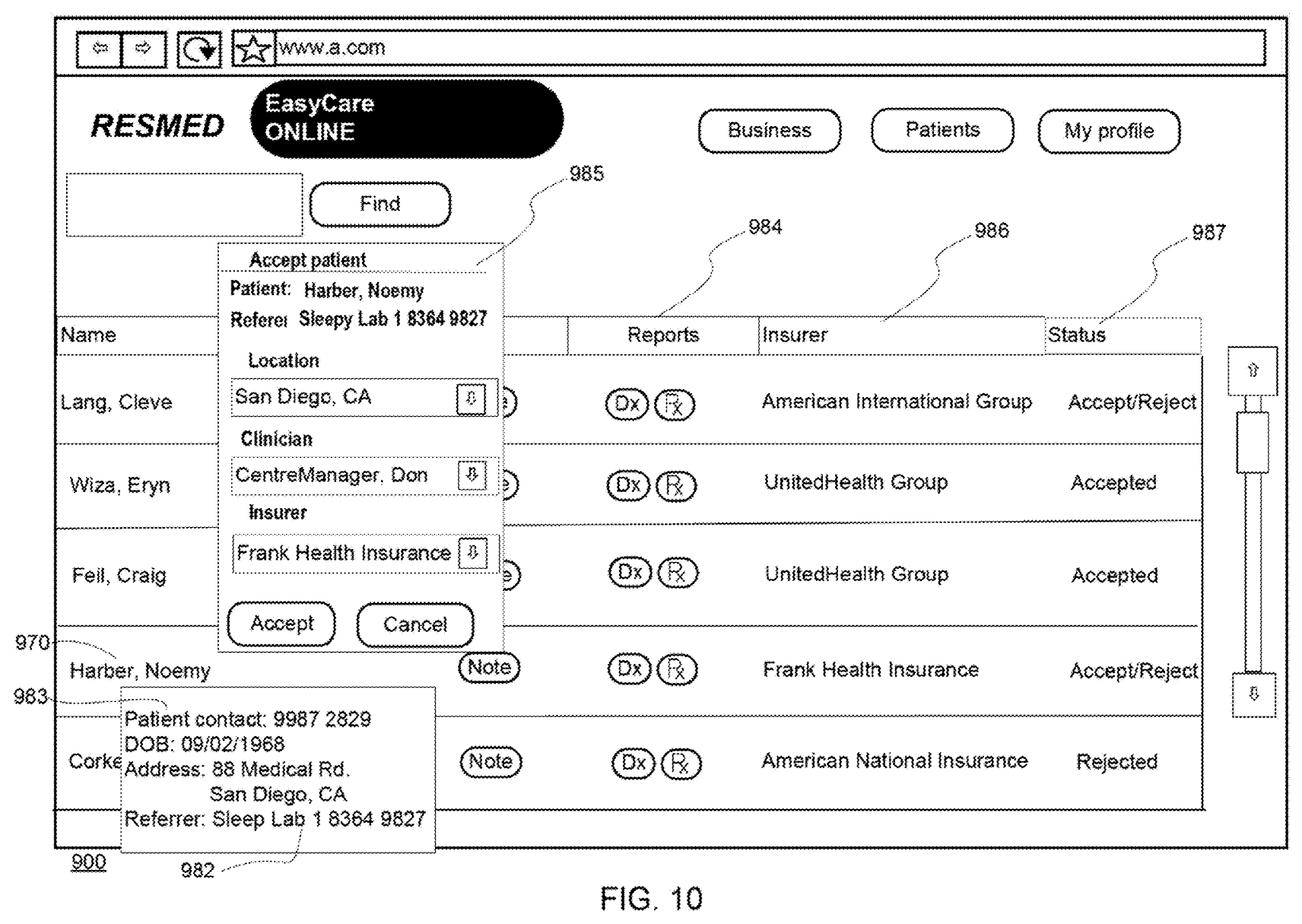
Figure 12:
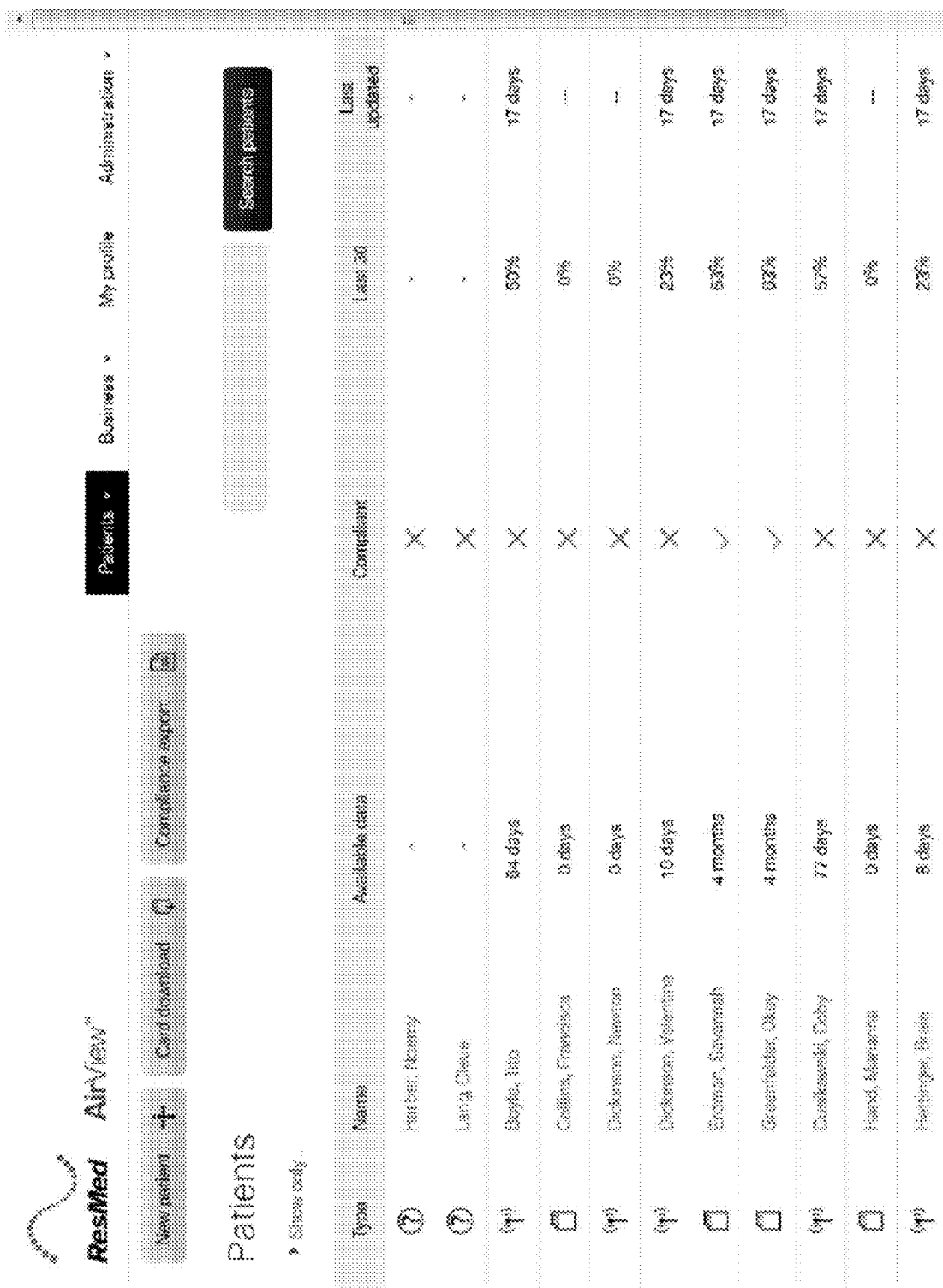

As shown in FIG. 10, Noemy Harber's patient record details are now visible to the administrative staff using therapy provider computer 102. After contacting the patient, such as by the website, e-mail, or phone, the administrator may schedule a time for a therapy provider to meet with the patient. For example, the administrator may click on Accept and use dialogue box 985 to assign the patient to a clinical user and transfer the new patient into the therapy provider's work queue. The therapy provider's work queue is shown in FIG. 12 as webpage 920. The work queue webpage may show compliance icons 1202 and noncompliance icons 1204 to indicate whether a patient is currently compliant with his or her prescribed therapy. The work queue may also indicate the last time the compliance data was updated, as well as statistics regarding the patient's usage of the therapy device. The work queue of webpage 920 may be securely accessed by a clinician, an administrator, or both. Secure access may include some form of protection to prevent unauthorized individuals from access patient data. For example, server 201 of FIG. 7 may require a password before transmitting patient data. Server 201 may also encrypt the transmitted data so as to prevent unauthorized devices from displaying the data.

Figure 13:
Figure 14:
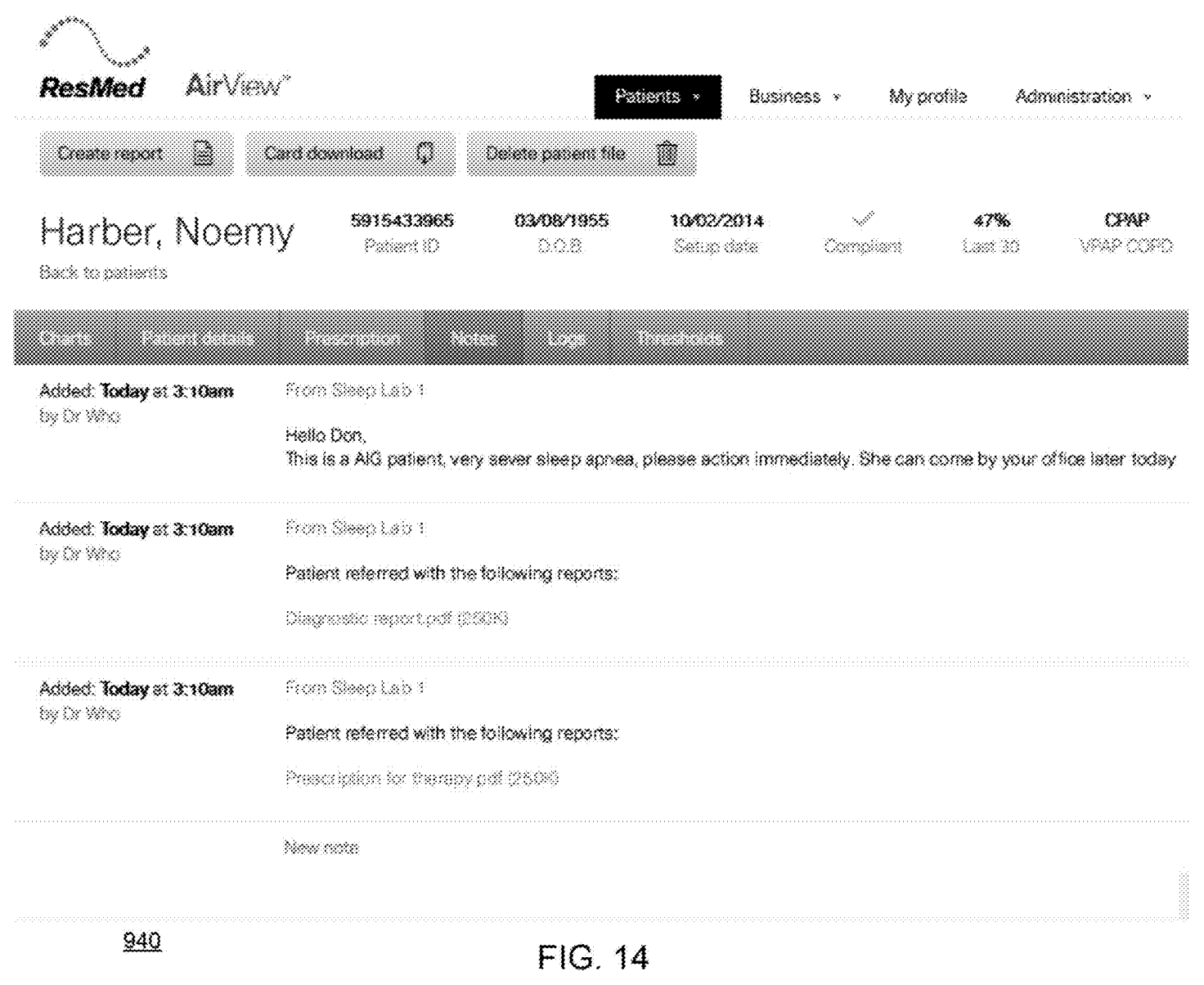

A healthcare professional may also assign and configure Noemy Harber's therapy device via webpage 920 shown in FIG. 12, and set her up for ongoing monitoring by clicking on her name and opening the patient record shown in FIG. 13 as webpage 930. As seen on webpage 930 within the patient record section, the patient information required to set up a patient for ongoing monitoring may be already pre-populated from the ECO database 233 with any patient data available from the diagnostic provider including patient demographics, insurance information and device therapy settings. As described above, a prescribed CPAP therapy device with a humidification unit is may be automatically assigned to the patient. In this way, healthcare professionals may quickly and easily set up patients on therapy without having to re-enter the patient data manually from paper prescriptions as well as reducing the percentage of patient who fail to present at the therapy provider for therapy. All therapy notes, prescriptions, and diagnostic reports may be viewed within the notes section of the patient record as shown in webpage 940 of FIG. 14.

Returning to FIG. 7, a therapy healthcare professional who accesses server 201 via therapy provider computer 102 may provide diagnostic and compliance summary reports, which have been generated by server 201, to the respective assessing entities. This can be performed by transmitting the diagnostic and/or compliance reports from therapy provider computer 102 to an external party, such as the reimbursing entity computer 103, via network 150. The diagnostic and/or compliance reports may be transmitted in any number of ways, including as part of an E-mail transmission. Alternatively, the diagnostic and/or compliance reports may be saved either at therapy provider computer 102 or server 201 and the assessing entity may send, via the reimbursing entity computer 103, a request for diagnostic and/or compliance reports to either computer 102 or server 201.

FIG. 15 provides a schematic representation for the system and methods described above. As seen in FIG. 15, a single patient record may be created, saved to a single data platform, updated and accessed by using a single software system, regardless of whether the patient is the diagnostic or the therapy stage of the patient management. In addition, the data platform may reside on multiple remote servers or on a single physical system of servers so as to allow for integrated electronic management of data relating to both the diagnostic stage and therapy stage. Medical practitioners from both the diagnostic management stage and the therapy management stage may be provided access to this record and can save and access relevant data associated with at least one of general patient data, diagnostic data, device usage data, compliance data, device parameters, diagnostic report, device prescription etc. This reduces the time and effort involved in creating multiple records, as well as minimises the likelihood of errors. The described system has the following features:

The capability to download to, upload from, view and analyse diagnostic data within the same software management tools and, in some cases, physical set of servers, as the therapy management stage data. This makes it much more convenient for both the diagnostic providers and the therapy providers, as they have a single point of access to the patient's data and do not need to use two different data platforms, have two different passwords etc. Here the term data platform is used broadly in relation to at least one of the hardware setup and the used software. The service providers from the reimbursement entity 103 also need to access both the diagnostic and the therapy data of the patient to evaluate whether the patient is compliant with the prescribed diagnostic or therapy requirements. Thus, they also benefit from the single password, the single point of entry and the use of a single data platform used for accessing both types of data.

The capability to upload diagnostic data, diagnostic reports, prescription information, as well as a therapy device usage and compliance data, directly into the original patient's therapy record created and populated in the diagnostics data management stage.

The capability to send device settings data from a prescription issued by a sleep physician directly to the diagnostic patient record, where it can be accessed and downloaded by the therapy provider without the need of manual rewriting or electronic re-creating of the record. This contrasts with the current practice of the patient having to personally take their prescription to the therapy provider or, at best, the diagnostic provider faxing or otherwise transferring the prescription to the therapy provider who then has to read the prescription and manually input the settings into the device. The proposed system allows the diagnostic provider to save the prescription in the patient record from where it is directly accessed by the therapy provider. Those settings can also be automatically downloaded to a card or sent wirelessly to the device upon device setup.

4.7 Other Remarks

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

It must be noted that as used herein and in the appended claims, the singular forms "a", "an", and "the" include their plural equivalents, unless the context clearly dictates otherwise.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative embodiments and that other arrangements may be devised without departing from the spirit and scope of the technology.

The invention claimed is:

1. A method for patient data processing during diagnosis and therapy of sleep disorder breathing, the method comprising:
   generating, by one or more computing devices, an electronic patient record for a patient;
   during a diagnostic stage of the patient, storing, by the one or more computing devices, diagnostic data from a diagnostic device in the electronic patient record;
   providing, by the one or more computing devices, a diagnostic provider with a first level of access to the electronic patient record;
   during a therapy stage of the patient, providing, by the one or more computing devices, a therapy provider with a second level of access to the electronic patient record, wherein providing the therapy provider with the second level of access to the electronic patient record comprises:
      generating, by the one or more computing devices, a graphical user interface for display of patient data;
      encrypting, by the one or more computing devices, patient data of the electronic patient record so as to prevent unauthorized devices from displaying the patient data; and
      transmitting, by the one or more computing devices, the encrypted patient data to at least a first computing device for display within the graphical user interface;
   transmitting, by the one or more computing devices, therapy settings to a therapy device, the therapy settings associated with at least one of a diagnostic report and a therapy prescription; and updating, by the one or more computing devices, the electronic patient record to include therapy data from the therapy device, wherein the first level of access comprises enabling the diagnostic provider to view and/or download the therapy data and preventing the diagnostic provider from modifying the therapy data and the second level of access comprises enabling the therapy provider to view and/or download the diagnostic data and preventing the therapy provider from modifying the diagnostic data.

2. The method of claim 1, wherein the method further comprises storing reports and prescriptions, generated during either the diagnostic stage or the therapy stage, in the electronic patient record.

3. The method of claim 1, wherein the method further comprises, when the diagnostic stage is at an end;

electronically notifying the therapy provider of a new patient, and providing the therapy provider with access to at least one of diagnostic data and prescription data of the patient.

4. The method of claim 1, wherein therapy settings from the therapy prescription are retrieved from the electronic patient record and used to automatically configure the therapy device for the patient.

5. The method of claim 4, wherein the automatic configuration is effected by way of a network connection or a memory card.

6. The method of claim 1, wherein providing the first level of access to the electronic patient record further comprises providing access to a first subset of the electronic patient record.

7. The method of claim 1, wherein providing the second level of access to the electronic patient record further comprises providing access to a second subset of the electronic patient record.

8. The method of claim 1, wherein, once the electronic patient record is created, medical practitioners associated with the diagnostic stage are provided with the first level of access to the electronic patient record and medical practitioners associated with the therapy stage are provided with the second level of access to the electronic patient record during both the diagnostic stage and the therapy stage.

9. The method of claim 1, wherein the diagnostic stage comprises receiving data from the diagnostic device and the therapy stage comprises receiving data from the therapy device, the therapy device being a flow generator for respiratory therapy.

10. An electronic system for integrated management of diagnostic and therapy data of a plurality of sleep disorder breathing patients:

one or more memories configured to store an electronic patient record comprising patient data;

one or more processors in communication with the one or more memories, the one or more processors configured to:

receive and store diagnostic data from a diagnostic device in the electronic patient record and provide a diagnostic provider with a first level of access to the electronic patient record during a diagnostic stage of patient management;

receive and store therapy data from a therapy device in the electronic patient record and provide a therapy provider with a second level of access to the electronic patient record during a therapy stage of the patient management, wherein the first level of access comprises enabling the diagnostic provider to view and/or download the therapy data and preventing the diagnostic provider from modifying the therapy data and the second level of access comprises enabling the therapy provider to view and/or download the diagnostic data and preventing the therapy provider from modifying the diagnostic data; and transmit therapy settings to a therapy device, the therapy settings associated with at least one of a diagnostic report and a therapy prescription, wherein the one or more processors are configured to provide the therapy provider with the second level of access to the electronic patient record by:

generating a graphical user interface for display of patient data;

encrypting patient data of the electronic patient record so as to prevent unauthorized devices from displaying the patient data; and transmitting the encrypted patient data to at least a first computing device for display within the graphical user interface.

11. The electronic system of claim 10, wherein at least one of the one or more processors are configured to store reports and prescriptions, generated during either the diagnostic stage or the therapy stage, in the electronic patient record.

12. The electronic system of claim 10, wherein when the diagnostic stage is at an end, at least one of the one or more processors is configured to enable sending of a notification to the therapy provider and provide access for the therapy provider to at least one of diagnostic, prescription and therapy data of the patient.

13. The electronic system of claim 10, wherein at least one of the one or more processors is configured to retrieve therapy settings from the therapy prescription of the electronic patient record and use it to automatically configure the therapy device for the patient.

14. The electronic system of claim 13, wherein the automatic configuration is effected by way of a network connection or a memory card.

15. The electronic system of claim 10, wherein providing the first level of access to the electronic patient record further comprises providing access to a first subset of the electronic patient record.

16. The electronic system of claim 10, wherein the providing the second level of access to the electronic patient record further comprises providing access to a second subset of the electronic patient record.

17. The electronic system of claim 10, wherein, once the electronic patient record is created, at least one of the one or more processors is configured to provide a provider associated with the diagnostic stage with the first level of access to the electronic patient record and to provide a provider associated with the therapy stage with the second level of access to the electronic patient record during both the diagnostic stage and the therapy stage.

18. The electronic system of claim 10, wherein the one or more processors are configured to process data from the diagnostic device, during the diagnostic stage, and from the therapy device, during the therapy stage, the therapy device being a flow generator used for respiratory therapy.

* * * * *